United States Patent
Steinmetz et al.

(10) Patent No.: US 10,590,394 B2
(45) Date of Patent: Mar. 17, 2020

(54) NON-COVALENT LOADING OF PLANT PICORNAVIRUS PARTICLES

(71) Applicant: CASE WESTERN RESERVE UNIVERSITY, Cleveland, OH (US)

(72) Inventors: Nicole Steinmetz, Cleveland, OH (US); Daniel Popkin, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/769,247

(22) PCT Filed: Feb. 18, 2014

(86) PCT No.: PCT/US2014/016925
§ 371 (c)(1),
(2) Date: Aug. 20, 2015

(87) PCT Pub. No.: WO2014/130454
PCT Pub. Date: Aug. 28, 2014

(65) Prior Publication Data
US 2015/0376578 A1      Dec. 31, 2015

Related U.S. Application Data

(60) Provisional application No. 61/767,994, filed on Feb. 22, 2013, provisional application No. 61/857,115, filed on Jul. 22, 2013.

(51) Int. Cl.
*A61K 39/12*       (2006.01)
*C12N 7/00*        (2006.01)
(Continued)

(52) U.S. Cl.
CPC ............... *C12N 7/00* (2013.01); *A61K 31/40* (2013.01); *A61K 31/473* (2013.01); *A61K 33/24* (2013.01);
(Continued)

(58) Field of Classification Search
None
See application file for complete search history.

(56) References Cited

U.S. PATENT DOCUMENTS

| | | | |
|---|---|---|---|
| 2006/0216238 A1* | 9/2006 | Manchester | A61K 47/48776 424/9.34 |
| 2012/0027727 A1 | 2/2012 | Hall et al. | |
| 2012/0039799 A1 | 2/2012 | Franzen et al. | |

FOREIGN PATENT DOCUMENTS

| | | |
|---|---|---|
| WO | 2008103920 A2 | 8/2008 |
| WO | 2012061445 A2 | 5/2012 |

OTHER PUBLICATIONS

Loo et al. Infusion of dye molecules into Red clover necrotic mosaic virus. Chem. Commun. (Camb) 2008; 1: 88-90.*

(Continued)

*Primary Examiner* — Janet L Andres
*Assistant Examiner* — Stuart W Snyder
(74) *Attorney, Agent, or Firm* — Tarolli, Sundheim, Covell & Tummino LLP

(57) ABSTRACT

A method of non-covalently loading a plant picornavirus is described. The method includes contacting a plant picornavirus in solution with a molar excess of a cargo molecule to load the plant picornavirus with the cargo molecule, and then purifying the loaded plant picornavirus. Examples of cargo molecules include imaging agents, antitumor agents, and antiviral agents. Loaded plant picornaviruses prepared in this manner can be used to delivering cargo molecule to cells.

13 Claims, 6 Drawing Sheets

(51) Int. Cl.
*A61K 35/76* (2015.01)
*A61K 31/40* (2006.01)
*A61K 31/473* (2006.01)
*A61K 33/24* (2019.01)
*A61K 47/46* (2006.01)

(52) U.S. Cl.
CPC .............. *A61K 35/76* (2013.01); *A61K 47/46* (2013.01); *C12N 2770/32041* (2013.01); *C12N 2770/32042* (2013.01)

(56) References Cited

OTHER PUBLICATIONS

Fraenkel-Conrat and Williams "Reconstitution of Active Tobacco Mosaic Virus from Its Inactive Protein and Nucleic Acid Components" Proc. Nat'l. Acad. Sci. 1955; 41: 690-8.*
Loo et al. Infusion of dye molecules into Red clover necrotic mosaic virus. Chem. Commun., 2008; 88-90.*
The Extended European Search Report for Application No. 14754692. 3, dated Jul. 15, 2016, pp. 1-8.
Loo et al., "Infusion of Dye Molecules into Red Clover Necrotic Mosaic Virus", Chem. Commun., 2008, pp. 88-90.
Yildiz et al., "Applications of Viral Nanoparticles in Medicine", Curr Opin Biotechnol., Dec. 2011, 22(6), pp. 901-908.
International Search Report for PCT/US2014/016925, dated May 13, 2014, 1 page.
Aljabali, Alaa AA, et al. "CPMV-DOX Delivers." Molecular pharmaceutics 10.1 (2012): 3-10.
Basu, Gautam, et al. "Metal binding to cowpea chlorotic mottle virus using terbium (III) fluorescence." JBIC Journal of Biological Inorganic Chemistry 8.7 (2003): 721-725.
Chatterji, Anju, et al. "New addresses on an addressable virus nanoblock: uniquely reactive Lys residues on cowpea mosaic virus." Chemistry & biology 11.6 (2004): 855-863.
Gomez-Ruiz, Santiago, et al. "On the discovery, biological effects, and use of cisplatin and metallocenes in anticancer chemotherapy." Bioinorganic chemistry and applications 2012 (2012).
Gonzalez, Maria J., et al. "Interaction of Cowpea mosaic virus (CPMV) nanoparticles with antigen presenting cells in vitro and in vivo." PLoS One 4.11 (2009): e7981.
Hovlid, Marisa L., et al. "Guiding plant virus particles to integrin-displaying cells." Nanoscale 4.12 (2012): 3698-3705.
Koudelka, Kristopher J., et al. "Endothelial targeting of cowpea mosaic virus (CPMV) via surface vimentin." PLoS Pathog 5.5 (2009): e1000417.
Lewis, John D., et al. "Viral nanoparticles as tools for intravital vascular imaging." Nature medicine 12.3 (2006): 354-360.
Loo, LiNa, et al. "Infusion of dye molecules into Red clover necrotic mosaic virus." Chemical communications 1 (2008): 88-90.

Perrault, Steven D., et al. "Mediating tumor targeting efficiency of nanoparticles through design." Nano letters 9.5 (2009): 1909-1915.
Plummer, Emily M., and Marianne Manchester. "Endocytic uptake pathways utilized by CPMV nanoparticles." Molecular pharmaceutics 10.1 (2012): 26-32.
Plummer, Emily M., et al. "Interaction of cowpea mosaic virus nanoparticles with surface vimentin and inflammatory cells in atherosclerotic lesions." Nanomedicine 7.6 (2012): 877-888.
Pokorski, Jonathan K., and Nicole F. Steinmetz. "The art of engineering viral nanoparticles." Molecular pharmaceutics 8.1 (2010): 29-43.
Prasuhn Jr, Duane E., et al. "Viral MRI contrast agents: coordination of Gd by native virions and attachment of Gd complexes by azide-alkyne cycloaddition." Chemical Communications 12 (2007): 1269-1271.
Raja, Krishnaswami S., et al. "Hybrid virus-polymer materials. 1. Synthesis and properties of PEG-decorated cowpea mosaic virus." Biomacromolecules 4.3 (2003): 472-476.
Ruoslahti, E. "Vascular zip codes in angiogenesis and metastasis." Biochemical Society Transactions 32.3 (2004): 397-402.
Sasikala, Wilbee D., and Arnab Mukherjee. "Molecular mechanism of direct proflavine—DNA Intercalation: evidence for drug-induced minimum base-stacking penalty pathway." The journal of physical chemistry B 116.40 (2012): 12208-12212.
Steinmetz, Nicole F., David J. Evans, and George P. Lomonossoff. "Chemical introduction of reactive thiols into a viral nanoscaffold: a method that avoids virus aggregation." ChemBioChem 8.10 (2007): 1131-1136.
Steinmetz, Nicole F., et al. "Cowpea mosaic virus nanoparticles target surface vimentin on cancer cells." Nanomedicine 6.2 (2011): 351-364.
Wellink, Joan. "Comovirus isolation and RNA extraction." Plant virology protocols. Humana Press, 1998. 205-209.
Wen, Amy M., et al. "Interior engineering of a viral nanoparticle and its tumor homing properties." Biomacromolecules 13.12 (2012): 3990-4001.
Wu, Zhuojun, et al. "Development of viral nanoparticles for efficient intracellular delivery." Nanoscale 4.11 (2012): 3567-3576.
Yildiz, Ibrahim, et al. "Infusion of imaging and therapeutic molecules into the plant virus-based carrier cowpea mosaic virus: cargo-loading and delivery." Journal of Controlled Release 172.2 (2013): 568-578.
Yildiz, Ibrahim, Sourabh Shukla, and Nicole F. Steinmetz. "Applications of viral nanoparticles in medicine." Current opinion in biotechnology 22.6 (2011): 901-908.
International Search Report and Written Opinion for PCT/US14/6925, dated May 13, 2014, pp. 2-9.
European Exam Report for Application No. 14754692.3-1112, dated Jun. 27, 2018.
European Exam Report for Application No. 14754692.3-1112, dated Feb. 15, 2019.

* cited by examiner

NON-COVALENT LOADING OF PLANT PICORNAVIRUS PARTICLES

CONTINUING APPLICATION DATA

This application claims the benefit of U.S. Provisional Application Ser. No. 61/767,994 filed Feb. 22, 2013, and U.S. Provisional Application Ser. No. 61/857,115, filed Jul. 22, 2013, which are incorporated by reference herein.

GOVERNMENT FUNDING

This work was supported, at least in part, by grant numbers NIBIB R00 EB009105, IK08 AI091641, and P30 AR039750 from the Department of Health and Human Services, National Institutes of Health, and Cancer Pharmacology training grant number NCI R25 CA148052. The United States government has certain rights in this invention.

BACKGROUND

The application of nanomaterials as carrier systems to deliver imaging reagents and/or drugs has gained momentum in the medical field. Nanoparticles are advantageous because their large surface-area-to-volume ratio allows functionalization with multiple different payloads and ligands. Nanoparticles are used to partition cargos between diseased and healthy tissue, ideally avoiding healthy tissues or at least minimizing the accumulation of toxic substances in healthy organs. Disease targeting (e.g., to cancer, inflammation, or infection), is achieved making use of the unique biological features that distinguish the microenvironment of diseased cells from healthy cells. For example, based on their size, nanoparticles home to solid tumors as a result of their leaky tumor blood vessels and the associated enhanced permeability and retention effects. Perrault et al., Nano Letters 9, 1909-1915 (2009). Other targeting strategies include the use of receptor-specific ligands to direct the nanocarrier to receptors selectively over-expressed at the target disease site. Ruoslahti E, Biochem Soc Trans, 32(Pt3), 397-402 (2004).

When it comes to cargo-loading and cargo-release, many different chemistries and mechanisms have been developed that control loading efficiency, affinity, and release rates; the choice of chemistry typically depends on the disease profile, cargo molecule, and carrier system of choice. Many different carrier systems are currently under investigation and development for drug delivery and tissue-specific imaging; each system has its advantages and disadvantages with regard to physiochemical properties, biodistribution and clearance, pharmacokinetic behavior, immunogenicity, and toxicity.

The inventors have focused on the development of bio-nanoparticles derived from plant viruses, also termed viral nanoparticles (VNPs). There are many novel types of VNPs under development, with those based on bacteriophages and plant viruses favored because they are considered safer in humans than mammalian viruses. Manchester M, Singh P, Adv Drug Deliv Rev 58(14), 1505-1522 (2006). Preclinical studies in mice have shown that plant viruses can be administered at doses of up to 100 mg ($10^{16}$ VNPs) per kg body weight without signs of toxicity. Singh et al., J Control Release, 120, 41-50 (2007). Like other protein-based nanomaterials they are immunogenic. However, strategies such as PEGylation can be used to overcome the immunogenicity of VNPs. Raja et al., Biomacromolecules, 3, 472-476 (2003). VNPs are genetically encoded and self-assemble into discrete and monodisperse structures with a precise shape and size. Many virus structures are understood at atomic resolution, allowing the development of protocols for high-precision VNP tailoring. This level of quality control cannot yet be achieved with synthetic nanoparticles. VNPs can be modified with targeting ligands and/or cargos using at least five approaches: genetic engineering, bioconjugate chemistry, self-assembly, mineralization, and infusion techniques. Pokorski J K, Steinmetz N F, Mol Pharm, 8, 29-43 (2011).

Cowpea mosaic virus (CPMV) is a plant picornavirus typically produced in black-eyed pea plants. CPMV capsids measure 30 nm in diameter and are comprised by 60 copies each of a small (S) and large (L) protein encapsulating a bipartite, single stranded, positive-sense RNA genome. CPMV has been extensively studied, developed, and tested for applications in the medical field. Bioconjugate chemistries on CPMV's exterior and interior surfaces are well established and its in vitro and in vivo properties are well understood. Wu et al., Nanoscale, 4, 3567-3576 (2012). CPMV naturally is taken up by mammalian cells through interactions with surface-expressed vimentin. Koudelka et al., PLoS Pathog, 5, e1000417 (2009). This unique property can be used to target CPMV to endothelial cells for vascular imaging and tumor vessel mapping (Lewis et al., Nature Medicine, 12, 354-360 (2006)), targeting vimentin-expressing cancer cells in vitro or in vivo (Steinmetz et al., Nanomedicine (Lond), 6, 351-364 (2011)), as well as targeting and imaging sites of inflammation, such as atherosclerotic plaques or infections of the central nervous system. Re-targeting of CPMV to receptors of interest can also be achieved through tailoring the surface chemistry with appropriate targeting ligands. Hovlid et al., Nanoscale 4, 3698-3705 (2012).

More recently, the application of CPMV as a carrier for drug delivery has been demonstrated. Cytotoxicity of CPMV nanoparticles chemically modified with multiple copies of the chemotherapeutic drug doxorubicin has been investigated. Aljabali et al., Mol. Pharm., 10, 3-10 (2013). However, multistep chemical modification procedures can be cumbersome, low yielding, and costly. Accordingly, there is a need for methods of using CPMV nanoparticles for drug delivery without requiring the use of multistep chemical modification procedures.

SUMMARY

The inventors have developed the cowpea mosaic virus (CPMV) platform as a tool for cargo-delivery by explored non-covalent cargo-loading strategies making use of the natural cargo, the nucleic acids. In some embodiments, the encapsidated nucleic acids act as a "sponge" to load imaging agents and drugs based on electrostatic interactions and/or affinity, as shown in FIG. 1, was evaluated. The non-covalent loading of several fluorophores and therapeutic molecules was demonstrated. Alternately, mechanisms that avoid the need for affinity with nucleic acid, such as infusion through gating, can also be used. Cargo-delivery in tissue culture and imaging and treatment using a panel of cancer cell lines were also carried out.

In one aspect, a method of loading a plant picornavirus by diffusion is provided. The method includes contacting a plant picornavirus in solution with a molar excess of at least 500 fold of a cargo molecule to load the plant picornavirus with the cargo molecule, and purifying the loaded plant picornavirus. In some embodiments, the cargo molecule has an affinity for nucleic acid, while in other embodiments other mechanisms (e.g., gating) can be used to encourage loading of the cargo molecule. In further embodiments, the plant picornavirus is a cowpea mosaic virus. In other embodiments, the cargo molecule is an imaging agent. In further embodiments, the cargo molecule is an antitumor agent or an antiviral agent. In yet further embodiments, the plant picornavirus is in contact with the cargo molecule for at least an hour, and the molar excess of cargo molecule is from about 5,000 to about 15,0000. In additional embodiments, purification of the loaded plant picornavirus includes the step of dialysis of the plant picornavirus solution.

In other embodiments, the method of loading a plant picornavirus also includes the step of chemically modifying the lysine side chains on the surface of the plant picornavirus. Examples of chemical modification include PEGylation or attachment of a cell penetrating peptide or targeting ligand. In further embodiments, the plant picornavirus is obtained from the extract of a plant infected by the plant picornavirus.

Another aspect of the invention provides a method of delivering a cargo molecule to a target cell, such as a vimentin-expressing cell. The method includes contacting the cell with a plant picornavirus loaded with the cargo molecule, prepared as described herein, wherein the cargo molecule is released within the cell subsequent to internalization of the loaded plant picornavirus by the cell. The cell can be either in vivo or in vitro. In some embodiments, the cell is a cancer cell. In other embodiments, the plant picornavirus is a cowpea mosaic virus. In further embodiments, the cargo molecule is an imaging agent, an antitumor agent, or an antiviral agent.

In other embodiments, the method of delivering a cargo molecule also includes the step of chemically modifying the lysine side chains on the surface of the plant picornavirus. Examples of chemical modification include PEGylation or attachment of a cell penetrating peptide or targeting ligand. In further embodiments, the plant picornavirus is obtained from the extract of a plant infected by the plant picornavirus. In other embodiments, the plant picornavirus loaded with the cargo molecule is provided as part of a pharmaceutical composition.

BRIEF DESCRIPTION OF THE FIGURES

FIG. 8 provides graphs showing that PF-429242 packaged CPMV inhibits S1P cleavage dependent viral replication. BHK-21 cells were infected at an MOI of 0.01 with either WT virus bearing the S1P recognition site RRLA (A) or mutant "Furin" virus (B). Mutant virus encodes a substitution at the S1P recognition site for RRLA→RRRR which is recognized by the furin protease and not by S1P. These recombinant viruses allow us to confirm specificity of PF429242 action for viral (vs. host) protein cleavage. The indicated amounts of the S1P inhibitor PF429242 or CPMV (empty or loaded with PF429242 to produce 20 M final concentration of the S1P inhibitor) were then added to the cultures after infection. Supernatant was collected and titered at the indicated time points. 1 of 2 similar experiments is shown.

DETAILED DESCRIPTION

Figure 1:
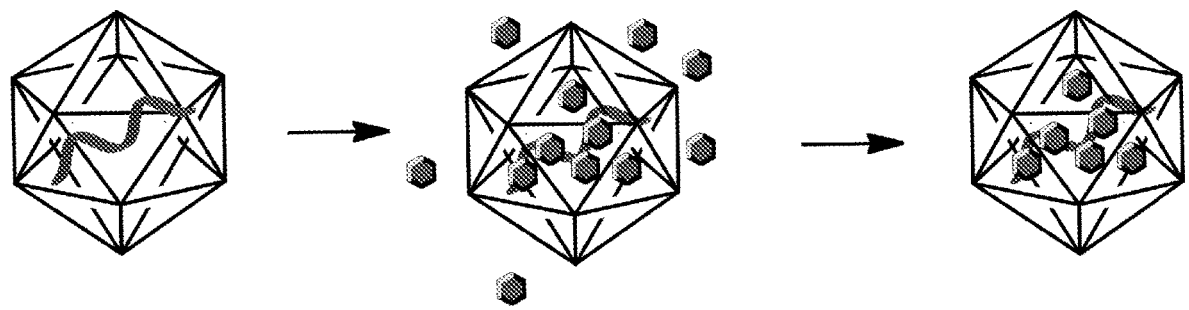
FIG. 1 provides a schematic view showing loading of a virus particle. On the left, a virus particle including a nucleic acid is shown. In the middle, the virus particle is shown in the presence of a substantial number of cargo molecules. Finally, on the right, a purified virus particle that has been successfully loaded with cargo molecules is shown.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

Contacting, as used herein, refers to causing two items to become physically adjacent and in contact, or placing them in an environment where such contact will occur within a short timeframe. For example, contacting a virus particle with a cargo molecule includes placing the virus particle and the cargo molecule in solution where they will rapidly associate through random motion within the solution.

"Targeting," as used herein, refers to the ability of loaded plant virus particles to be delivered to and preferentially accumulate in target tissue (e.g., a tumor) or type of cell (e.g., an immune cell) in a subject.

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor. "Apa" is aminopentanoic acid.

A "nucleic acid" refers to a polynucleotide and includes polyribonucleotides and polydeoxyribonucleotides.

The term "antibody" as used herein refers to an immunoglobulin, whether natural or partly or wholly synthetically produced. The term also covers any polypeptide, protein or peptide having a binding domain that is, or is homologous to, an antibody binding domain. These can be isolated from natural sources, or may be partly or wholly synthetically produced. Examples of antibodies are intact immunoglobulin molecules, as well as to fragments thereof, such as Fab, $F(ab')_2$, Fv fragments, and single chain variable fragments (scFv), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of an Fab or other immunoglobulin expression library, and suitable derivatives.

As used herein, an antibody "specifically binds," meaning that the antibody preferentially binds a target structure, or subunit thereof, but binds to a substantially lesser degree or does not bind to a biological molecule that is not a target structure. Antibodies that specifically bind to a target structure, or subunit thereof, do not cross-react with biological molecules that are outside the target structure family.

As used herein, "internalization" refers to a process by which a plant picornavirus particle binds to a target element on the outer surface of the cell membrane and the resulting complex is internalized by the cell, i.e., moves into the cytoplasm or vesicle compartment of the cell without causing irreparable damage to the cell membrane. Internalization may be followed up by dissociation of the resulting complex within the cytoplasm. The target element, along with the molecule or the construct, may then undergo degradation within the cell or localize to a specific cellular compartment. Preferably, the plant picornavirus is localized to the endolysososme, where the carrier is degraded and the cargo released. Targeting ligands may also be employed to target specific intracellular organelles or control the intracellular trafficking and fate of the nanoparticle carrier.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective imaging or treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

In one aspect, the present invention provides a method of loading a plant picornavirus. A schematic view showing the loading of a plant picornavirus particle is shown in FIG. 1. The method includes the steps of contacting a plant picornavirus in solution with a significant molar excess of a cargo molecule in order to load the plant picornavirus with the cargo molecule, and then purifying the loaded plant picornavirus. A plant picornavirus loaded with cargo molecule is referred to herein as a "loaded picornavirus," a "loaded particle," or a "loaded plant pincornavirus particle." A loaded picornavirus is a plant picornavirus in which one or more cargo molecules have associated (e.g., with the nucleic acid) within the virus particle in a non-covalent manner. Preferably, the plant picornavirus is loaded with a plurality, or a substantial number of cargo molecules. For example, in some embodiments, from about 50 to about 300 cargo molecules are loaded, while in other embodiments from about 100 to about 200 cargo molecules are loaded.

The plant picornavirus can be obtained from the extract of a plant infected by the plant picornavirus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998), the disclosure of which is incorporated herein by reference.

The plant picornavirus is loaded with the cargo molecule in a non-covalent manner. In some embodiments, the cargo molecule associates with the nucleic acid within the plant picornavirus, inside the viral particle capsid. While not intending to be bound by theory, it appears that the cargo molecule associates with the nucleic acid within the plant picornavirus as a result of the affinity of the cargo molecule for the nucleic acid. Affinity is the tendency of a compound to naturally associate with another object (e.g., a nucleic acid). Affinity is influenced by non-covalent intermolecular interactions between the compound and the object, such as hydrogen bonding, electrostatic interactions, hydrophobic interactions, and Van der Waals forces. As used herein, affinity refers to an interaction between a compound and another object having a dissociation constant of at least one micromolar. However, cargo molecules lacking affinity for nucleic acid can be loaded through gating, in which the virus capsid is exposed to a alkaline solution, which results in swelling and pore opening; the drug is then infused, buffer exchange to neutral solution traps the cargo inside the capsid.

The plant picornavirus can be loaded with the cargo molecule in a non-covalent manner relying on simple diffusion from solution into the picornavirus particle by contacting the plant picornavirus with a solution including the cargo molecule. To allow the cargo molecule to diffuse into the plant picornavirus particles, sufficient time should be provided for the diffusion to occur. In various embodiments, at least 5 minutes, at 10 minutes, at least 30 minutes, at least one hour, at least 4 hours, at least 8 hours, or at least 24 hours may be provided to allow diffusion into the plant picornavirus particle. In addition, it is preferable that a molar excess of the cargo molecule be provided in the solution to encourage diffusion into the plant picornavirus particle. The molar excess is the amount of cargo molecule relative to the amount of plant picornavirus present on a per-particle or compound basis. In some embodiments, the molar excess is at least about 500 fold. For example, a molar excess of about 500 to 1000 cargo molecules to plant picornavirus particles, an excess of about 1,000 to 5,000, an excess of about 5,000 to 15,000, or an excess of about 15,000 to 50,000 cargo molecules to plant picornavirus particles may be used.

The method of preparing a loaded plant picornavirus may also includes the step of purifying the plant picornavirus from the solution in which diffusion into the virus particle was carried out. In some embodiments, the plant picornavirus is purified from the solution by dialysis of the plant picornavirus solution. For example, dialysis can be carried out using dialysis membranes. In this procedure, the plant picornavirus and a bathing solution containing the cargo is placed in a dialysis bag with appropriate molecular weight cut off (e.g., about 1,000 Da, about 10,000 Da, or about 100,000 Da) so that non-associated, free cargo molecules can freely diffuse through the pores and are removed. Preferably, the dialysis bag is placed in a large volume of buffer (e.g., 100× the volume of the reaction of larger), and buffer is replaced a plurality of times (e.g., at least three times). The plant picornaviruses, which are larger and have a molecular weight in the megadalton range, are retained within the dialysis membrane. Repeated washing steps and buffer replacement can be used to ensure that all excess cargo is removed from the solution Subsequent to purification (e.g., by dialysis), the loaded plant picornavirus particles can be further purified by centrifugation. For example, the particles can be purified using a sucrose gradient or size exclusion chromatography using fast protein liquid chromatography (e.g., using an Äkta Purifier and Superose 6 column). Depending on the conditions and plants used, the method of preparing loaded plant picornavirus can provide from about 0.1 to about 5 mg of virus particles per plant, or in some embodiments from about 0.5 to about 2 mg, or from about 0.5 mg to about 1 mg.

Use of the terms "virus" and "virus particle" are used interchangeably herein. Virus particles include a number of capsid proteins that are assembled to form a protein cage, within which is the nucleic acid encoding the virus. Note that the viruses and virus particles described herein are presumed to include a nucleic acid within the protein cage, unless specifically stated to the contrary. However, the presence of a nucleic acid within the virus is not required in embodiments where a mechanism other than affinity for the nucleic acid is used to facilitate loading of the cargo molecule into the virus particle. While the nucleic acid will typically be the nucleic acid encoding the virus, in some embodiments the viral nucleic acid may have been replaced with exogenous nucleic acid. In some embodiments, the nucleic acid is RNA, while in other embodiments the nucleic acid is DNA.

Plant picornaviruses are used as the virus particle into which the cargo molecules are loaded. A plant picornavirus is a virus belonging to the family Secoaviridae, which together with mammalian picornaviruses belong to the order of the Picornavirales. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus comovirus. A preferred example of a comovirus is the cowpea mosaic virus particles.

Cargo Molecules

A variety of different types of cargo molecules can be loaded into the plant picornavirus particles. The main limitation on cargo molecules is that they must be sufficiently small to fit within the icosohedral capsid (i.e., have a size of 10 nm or less). Cargo molecules are typically small organic molecules having a size of 0.1-10 nm Cargo molecules also preferably have a molecular weight ranging from about 100 to about 5000 daltons, with some embodiments being directed to cargo molecules having a weight ranging from about 200 to about 4000 daltons, or from about 400 to about 3000 daltons. Examples of preferred cargo molecules are imaging agents and therapeutic agents such as antiviral agents or antitumor agents.

In addition to being sufficiently small to fit within the icosohedral capsid, in some embodiments it is preferable that the cargo molecules have an affinity for the nucleic acid within the virus particle. An example of cargo molecules having an affinity for the nucleic acid are cargo molecules having a positive charge. One skilled in the art can readily determine whether a cargo molecule has affinity for the nucleic acid (e. g., RNA) within a plant virus particle. For example gel mobility shift assays, oligonucleotide crosslinking assays, optical absorbance and fluorescence assays, calorimetric assays, and/or surface Plasmon resonance assays to determine the association and dissociation kinetics and affinities of cargo molecules for nucleic acids. Furthermore, any drug or imaging agent exhibiting low affinity can be readily modified with a small, positively charged tag or complementary oligonucleotide to bind to the plant picornavirus nucleic acid. For some embodiments, it is also preferable that the cargo molecules interact with nucleic acids in a reversible manner, in order to facilitate release of the cargo molecules in the target tissue subsequent to internalization.

In some embodiments, the cargo molecule is an imaging agent. Examples of imaging agents include fluorescent imaging agents, cancer imaging agents, magnetic resonance imaging agents, nuclear medicine imaging agents, positron emission tomography imaging agents, and X-ray imaging agents. Because cargo molecules, as defined herein, are restricted to small organic molecules, inorganic imaging agents such as barium are not included in the category of imaging agents which can be delivered by the present invention. Examples of imaging agents include diatrizoic acid, fluoresceine isothiocyanate, $^{18}$F-fluoromisonidazole, 3'-deoxy-3'-[$^{18}$F]fluorothymidine, $^{18}$F-fluorodeoxyglucose, $^{64}$Cu-diacetyl-bis(N$^4$-methylthiosemicarbazone), iohexol, Tc-99mW-(2-methoxy-2-methyl-propyl)methanimine]and derivatives thereof with derivatives being compounds modified with a small, positively charged tag or complementary oligonucleotide to provide increased affinity. A comprehensive review of imaging agents can be found in the Molecular Imaging and Contrast Agents Database (MICAD), developed by the National Center for Biotechnology Information, which is incorporated herein by reference.

In other embodiments, the cargo molecule is a therapeutic agent. Examples of therapeutic agents include cardiovascular drugs (e.g., antihypertensive drugs, antiarrhythmic agents, and diuretics), neuropharmaceuticals (e.g., analgesics, anesthetics, and antipsychotics), gastrointestinal drugs (e.g., anti-ulcer drugs, antiemetics, and gastroprokinetic agents), respiratory tract agents (e.g., anthasthamtic or antiallergic drugs), antiinfective agents (antibiotics, antimycotics, and antiviral agents), endocrine-affecting drugs (e.g., steroids, hormones, and contraceptives), anti-inflammatory drugs, immunosuppressant drugs, and antitumor agents.

Because of the ability of plant picornavirus particles to associate with tumor cells, a preferred type of therapeutic agent for use as a cargo molecule are antitumor agents. Examples of antitumor agents include angiogenesis inhibitors such as angiostatin K1-3,DL-α-difluoromethyl-ornithine, endostatin, fumagillin, genistein, minocycline, staurosporine, and (±)-thalidomide; DNA intercalating or crosslinking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives (as defined for imaging agents) thereof. In some embodiments, the antitumor agent is a small molecular antitumor agent.

In other embodiments, the cargo molecule is an antiviral agent. The inventors have shown that plant picornaviruses such cowpea mosaic virus have a natural affinity for certain cells of the immune system such as macrophages and dendritic cells, which can be the natural target for viruses such as cowpea mosaic virus. Accordingly, plant picornavirus particles loaded with cargo molecule will naturally deliver antiviral agent to macrophages and dendritic cells. Examples of antiviral agents include abacavir, acyclovir, adefovir, amantadine, amprenavir, ampligen, arbidol, atazanavir, atripla, balavir, boceprevirertet, cidofovir, combivir, dolutegravir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon types I-III, lamivudine, lopinavir, loviride, maraviroc, moroxydine, methisazone, nelfinavir, nevirapine, nexavir, oseltamivir (Tamiflu), peginterferon alfa-2a, penciclovir, peramivir, PF-429242, pleconaril, podophyllotoxin, raltegravir, ribavirin, rimantadine, ritonavir, pyramidine, saquinavir, sofosbuvir, stavudine, tea tree oil, telaprevir, tenofovir, tenofovir disoproxil, tipranavir, trifluridine, trizivir, tromantadine, truvada, traporved, valaciclovir (Valtrex), valganciclovir, vicriviroc, vidarabine, viramidine, zalcitabine, zanamivir (Relenza), and zidovudine.

Modified Plant Picornaviruses

In some embodiments, the surface of the plant picornavirus is modified. For example, the plant picornavirus can be modified to include PEGylation, cell penetrating peptides, or one or more targeting ligands. In further embodiments, the plant picornavirus can be modified to include a covalently bound imaging agent or therapeutic agent. For example, a plant picornavirus can be loaded with an antitumor agent, and an imaging agent can be covalently bound to the loaded plant picornavirus to track delivery of the drug to the tumor site. The plant picornavirus can be modified either before loading with cargo molecules, or after loading with cargo molecules. Targeting ligands can be attached to the outside of the plant picornavirus in order to guide the loaded plant picornavirus particles to a particular target tissue, such as tumor tissues. Examples of targeting ligands include peptide ligands (e.g., RGD, bombesin, or GE11), vitamins such as folic acid, and other tumor-homing proteins such as transferring, as well as and antibodies such as Herceptin or any other antibody with tumor-specific properties, and DNA-, RNA-, or PNA-based aptamers that specifically bind to an antigen present on the target tissue, such as a tumor antigen. Cell penetrating peptides can also be attached to the outside of the plant picnornavirus, and encourage internalization of the loaded plant picornavirus. Cell penetrating peptides are generally relatively short, amphipathic peptides. Examples of cell penetrating peptides include TAT sequence or polyArginine peptides.

In general, modifying compounds can be conjugated to the plant picornavirus by any suitable technique, with appropriate consideration of the need for pharmacokinetic stability and reduced overall toxicity to the patient. The term "conjugating" when made in reference to an agent and a plant picornavirus particle as used herein means covalently linking the agent to the virus subject to the single limitation that the nature and size of the agent and the site at which it is covalently linked to the virus particle do not interfere with the biodistribution of the modified virus.

An agent can be coupled to a plant picornavirus particle either directly or indirectly (e.g. via a linker group). In some embodiments, the agent is directly attached to a functional group capable of reacting with the agent. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can serve to increase the chemical reactivity of a substituent on either the agent or the virus particle, and thus increase the coupling efficiency. A preferred group suitable as a site for attaching agents to the virus particle is lysine residues present in the viral coat protein.

Suitable linkage chemistries include maleimidyl linkers and alkyl halide linkers and succinimidyl (e.g., N-hydroxysuccinimidyl (NHS)) linkers (which react with a primary amine on the plant picornavirus particle). Several primary amine, sulfhydryl groups, and carboxylate or tyrosine groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be affected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, the plant picornavirus particles are modified by PEGylation. PEGylation can be useful to decrease the immunogenicity and clearance of the loaded plant picornavirus particles. PEGylation is the process of covalent attachment of polyethylene glycol (PEG) polymer chains to a molecule such as a plant picornavirus particle. PEGylation can be achieved by incubation of a reactive derivative of PEG with the plant picornavirus particle. The covalent attachment of PEG to the plant picornavirus particle can "mask" the agent from the host's immune system.

The first step of PEGylation is providing suitable functionalization of the PEG polymer at one or both terminal positions of the polymer. The chemically active or activated derivatives of the PEG polymer are prepared to attach the PEG to the plant picornavirus particles. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

Medical and Therapeutic Use of Loaded Plant Picornavirus Particles

Another aspect of the invention provides a method of delivering a cargo molecule to a target cell. Examples of target cells include tumor cells, cells involved in inflammation, certain immune cells such as dendritic cells and macrophages, and/or vimentin-expressing cells. Vimentin-expressing cells are a preferred target because cowpea mosaic virus particles have an affinity for vimentin, which also facilitates internalization of the loaded virus particles. Accordingly, in some embodiments, the plant picornavirus is a cowpea mosaic virus. However, virus particles can be modified for targeting to a variety of different issues by modifying the plant picornavirus to include a targeting ligand such as antibodies that specifically bind to an antigen present on the target tissue. The method includes contacting the cell with a plant picornavirus loaded with the cargo molecule, prepared as described. Upon contact with the cell, the cargo molecule is typically released within the cell subsequent to internalization of the loaded plant picornavirus.

Various different embodiments of the method of delivering a cargo molecule using plant picornavirus particles loaded with the cargo molecule by diffusion are envisioned. In some embodiments, the cargo molecule is an antitumor agent, while in other embodiments the cargo molecule is an antiviral agent or an imaging agent. In some embodiments, the cell contacted with the loaded plant picornavirus is a cancer cell. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the loaded picornavirus particles including antitumor compounds are used to treat or image cancer tissue selected from the group consisting of colon cancer, brain cancer, breast cancer, fibrosarcoma, and squamous carcinoma.

Selectivity for a specific type of cancer cell or a specific group of types of cancer cells can be conferred by modifying the plant picornavirus to include a targeting ligand (e.g., an antibody), since the targeting ligand binds selectively to a structure present on the surface of a specific type of cancer cell or a specific group of types of cancer cells. However, as a reminder, such targeting is not necessary for all embodiments, due to the inherent ability of plant picornavirus particles to associate with tumor cells. The choice of targeting ligand incorporated on the construct will ultimately help determine the specificity of the construct. By identifying the target structure of interest based on the knowledge available about cancer cells and their biological structure, one skilled in the art would be able to choose the desired targeting ligand that binds the target structure selectively.

In other embodiments, the plant picornavirus has been chemically modified. Modification can be achieved using the methods of modification described herein, such as attachment of groups to lysine side chains on the surface of the plant picornavirus. Examples of modification include any of the types of modification described herein. For example, the chemical modification of the plant picornavirus can include PEGylation of the plant picornavirus, attachment of a cell penetrating peptide to the plant picornavirus, or the covalent attachment of an imaging agent or therapeutic agent.

In some embodiments, the method includes use of a plant picornavirus particle that has been loaded with an imaging agent. In such embodiments, the method may also includes the step of imaging the target tissue (e.g., tumor) in the subject using an imaging device and an effective amount of a plant picornavirus is administered subsequent to administering an effective amount of the loaded plant picornavirus to the subject. Examples of imaging methods include computed tomography, positive emission tomography, magnetic resonance imaging, and optical or fluorescence imaging.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

The compositions of the invention can be used for the imaging and detection of target cells in cell cultures and in vivo. The compositions of the invention can also be used for the imaging and detection of target cells in organs and tissues ex vivo. Examples of target cells include cancer cells, cells involved in inflammation, immune cells such as dendritic cells and macrophages, and vimentin-expressing cells. The compositions of the invention can also be used for killing or preventing the growth of cancer cells, provided that the compositions include a therapeutic agent that is capable of killing or stopping the growth of cancer cells once internalized.

When used to detect or image cancer cells in a cell culture, one skilled in the art should be able to vary the exposure time, the amount of loaded plant picornavirus and the final concentration to optimize the detection or imaging desired. Other experimental parameters may be varied to achieve the other effect, depending on the specific experiment conducted, and identification of such parameters should involve minimal experimentation by those skilled in the art.

In many embodiments, the loaded plant picornavirus is used to treat or image cells that are in vivo. However, it should be appreciated that all the preceding and following therapeutic applications may also be performed in an "ex vivo" manner. In this case, a tissue or organ in which detection or killing of cancer cells is desired may be removed from an organism, under conditions which allows the tissue or organ to remain viable and with minimal alteration of the natural conditions of the tissue or organism.

The procedure should usually be conducted under sterile conditions to minimize possibility of contamination. The tissue or organ may be exposed to the composition of the invention for a variable amount of time, from minutes to days. The compositions of the invention may be provided as suspensions, powders, pastes or other suitable presentations, and the mode of contact between the composition of the invention and the tissue or organ should be such that detection or killing of cancer cells is achieved. Those skilled in the art should be able to determine the optimal contact time without undue experimentation. Once the desired detection or killing of cancer cells is achieved, the tissue or organ may be returned to the original organism or to another organism in need to such tissue or organ. Transplantations should proceed following the procedures known by those skilled in the art.

Dosage and Formulation of Loaded Plant Picornavirus Particles

When used in vivo, the constructs of the invention are preferably administered as a pharmaceutical composition, comprising a mixture, and a pharmaceutically acceptable carrier. The loaded picornavirus may be present in a pharmaceutical composition in an amount from 0.001 to 99.9 wt %, more preferably from about 0.01 to 99 wt %, and even more preferably from 0.1 to 95 wt %.

The loaded plant picornavirus particles, or pharmaceutical compositions comprising these particles, may be administered by any method designed to provide the desired effect. Administration may vary depending on whether or not the loaded plant picornaviruses are being used for imaging or for a therapeutic effect. Administration may occur enterally or parenterally; for example orally, rectally, intracisternally, intravaginally, intraperitoneally or locally. Parenteral and local administrations are preferred. Particularly preferred parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device. Particularly preferred local administrations include powders, ointments, suspensions and drops.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The pharmaceutical compositions of this invention are particularly useful for parenteral administration, such as administration into a body cavity or lumen of an organ. The compositions for administration will commonly comprise a suspension of the loaded picornavirus in a pharmaceutically acceptable carrier, preferably an aqueous carrier. A variety of aqueous carriers can be used, e.g., buffered saline and the like. These suspensions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The amount of the loaded picornavirus in these formulations can vary widely, and will be selected primarily based on fluid volumes, viscosities, body weight and the like in accordance with the particular mode of administration selected and the subject's needs.

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Suitable doses can vary widely depending on the therapeutic or imaging agent being used. A typical pharmaceutical composition for intravenous administration would be about 0.1 mg to about 10 g per subject per day. However, in other embodiments, doses from about 1 mg to about 1 g, or from about 10 mg to about 1 g can be used. Methods for preparing parenterally administrable compositions will be known or apparent to those skilled in the art and are described in more detail in such publications as Remington's Pharmaceutical Science, 15th ed., 1980, Mack Publishing Company, Easton, Pa.

Single or multiple administrations of the compositions may be administered depending on the dosage and frequency as required and tolerated by the subject. In any event, the administration regime should provide a sufficient quantity of the composition of this invention to effectively treat the subject.

The formulations may be conveniently presented in unit dosage form and may be prepared by any of the methods well known in the art of pharmacy. Preferably, such methods include the step of bringing the loaded plant picornavirus into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated virus carrier can be administered as a single dose or in multiple doses.

For plant picornavirus particles loaded with a therapeutic agent such as an antitumor or antiviral agent, an exemplary treatment regime entails administration once per every two weeks or once a month or once every 3 to 6 months. The loaded plant picornavirus is usually administered on multiple occasions. Alternatively, the loaded plant picornavirus can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of the disease.

One skilled in the art can readily determine an effective amount of loaded picornavirus to be administered to a given subject, by taking into account factors such as the size and weight of the subject; the extent of disease penetration; the age, health and sex of the subject; the route of administration; and whether the administration is local or systemic. For example, to provide a dose of 10 mg doxorubicin per kg patient, one would need to administer 8000 mg (8 g) if the patient weights 80 kg. In the case where the construct comprises a therapeutic agent meant to selectively kill cancer cells, the amount of loaded picornavirus to be administered to a subject depends upon the mass of cancer cells, the location and accessibility of the cancer cells, and the degree of killing of cancer cells caused by the therapeutic agent. Those skilled in the art may derive appropriate dosages and schedules of administration to suit the specific circumstances and needs of the subject. For example, suitable doses of loaded picornavirus to be administered can be estimated from the volume of cancer cells to be killed.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

Useful dosages of the active agents can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the loaded plant picornavirus vary depending upon many different factors, including means of administration, target site, physiological state of the patient, whether the patient is human or an animal, other medications administered, and whether treatment is prophylactic or therapeutic.

The following examples of methods are included for purposes of illustration and are not intended to limit the scope of the invention.

EXAMPLES

Example 1: Loading CPMV Nanoparticles

Methods

CPMV propagation and purification: Black-eyed peas #5 (*Vigna unguiculata*) were inoculated with 20 ng/ml CPMV in 0.1 M potassium phosphate buffer (pH 7.0) and propagated for 18 20 days using established procedures. Wellink J., Meth Mol Biol, 8, 205-209 (1998). Virus concentration in plant extracts was determined by UV/visible spectroscopy and virus integrity was determined by size exclusion chromatography and UV/visible spectroscopy. A pure CPMV preparation has an absorbance ratio of A260 nm:A280 nm of 1.7±0.1. Empty CPMV (eCPMV) were provided by a colleague. Saunders et al., Virology 393(2), 329-37 (2009).

Cargo-loading via infusion: A solution of CPMV (at 1 mg mL$^{-1}$ in 0.1 M potassium phosphate buffer pH 7.4, in the following referred to as KP buffer) was mixed with a 10,000-fold molar excess of the desired cargo molecule (see below) for 1 hour at room temperature in the dark. (The molecular weight of CPMV is 5.6×10$^6$ g mol$^{-1}$) Concentration curves were evaluated to determine the optimal excess to achieve efficient loading; CPMV was incubated with a molar excess 1,000, 2,000, 5,000, 10,000, and 50,000 cargo molecules per one CPMV. Time course studies were also conducted and it was found the loading does not improve after one hour of incubation. The following cargo molecules were studied: DAPI (4',6-diamidino-2-phenylindole dihydrochloride, MP Biomedicals). Propidium iodide (3,8-diamino-5-[3-(diethylmethylammonio)propyl]-6-phenyl-phenanthridinium diiodide, Sigma Aldrich), acridine Orange (3,6-bis(dimethylamino)acridinium chloride, MP Biomedicals), CDDP (cisplatin or cis-dichlorodiammine platinum (II), Sigma Aldrich), and proflavine (PF, acridine-3,6-diaminoacridine hydrochloride, Sigma Aldrich). The reaction was then purified to remove cargo-loaded CPMV from excess reagents through extensive dialysis (Spectra/Por2, MWCO 12-14 KDa, Spectrum Laboratories) and multiple rounds of centrifuge filtration using spin columns (Amicon, MWCO 10 KDa). The cargo-loaded CPMV product was characterized using a combination of SEC, UV/Visible spectroscopy, and native and denaturing gel electrophoresis, and inductively coupled plasma optical emission spectroscopy (ICP-OES).

Covalent bioconjugation of CPMV: CPMV was labeled at surface -exposed lysine residues using N-hydroxysuccinimide (NHS) active AlexaFluor 555 (A555, Invitrogen) or NHS activated Oregon Green 488 (O488, Invitrogen). Chemical modification was performed as a subsequent step, after cargo infusion. NHS-A555 or O488 in DMSO was added to CPMV (at 2 mg/mL in KP buffer) at a molar excess of 2000 NHS-A555/O488: 1 CPMV; the final DMSO concentration was adjusted to 10% by volume, the protein concentration was kept at 1 mg/mL. The mix was reacted for two hours at room temperature with agitation in the dark. The reaction mix was purified through dialysis and spin filters as described above.

Size exclusion chromatography (SEC): All CPMV nanoparticle preparations were analyzed by SEC using a Superose6 column on the ÄKTA Explorer chromatography system (GE Healthcare). Samples (100 μl of 1 mg/mL) were analyzed at a flow rate of 0.5 mL/min, using 0.1 M potassium phosphate buffer (pH 7.4).

UV/visible spectroscopy: A NanoDrop Spectrophotometer was used to measure the UV/visible spectra of native and modified CPMV nanoparticles. The degree of dye-loading was determined based on the concentration of dye:CPMV making use of Beer Lambert law and the dye and CPMV-specific extinction coefficients: CPMV: $\varepsilon(260$ nm$)=8.1$ mL mg$^{-1}$ cm$^{-1}$, molecular weight of CPMV=5.6× 10$^6$ g mol$^{-1}$, DAPI: $\varepsilon(358$ nm$)=24,000$ M$^{-1}$cm$^{-1}$ PI: $\varepsilon(493$ nm$)=5,900$ M$^{-1}$cm$^{-1}$, AO: $\varepsilon(470$ nm$)=43,000$ M$^{-1}$ cm$^{-1}$, PF: $\varepsilon(445$ nm$)=40,000$ M$^{-1}$cm$^{-1}$, A555: $\varepsilon(555$ nm$)=155,000$ M$^{-1}$cm$^{-1}$, O488: $\varepsilon(496$ nm$)=75,000$ M$^{-1}$cm$^{-1}$. It should be noted that the extinction coefficients may change in different chemical environments; degree of dye-loading is thus an approximation.

Native and denaturing gel electrophoresis: CPMV nanoparticles were analyzed on native and denaturing gels. 5-10 μg sample was analyzed on 1.2% agarose gel in 1× TBE buffer, running buffer was 1× TBE. TBE=45 mM Tris, 45 mM boric acid, 1.25 mM EDTA in MilliQ water. Protein subunits were analyzed on denaturing 4-12% NuPAGE gels (Invitrogen) using 1x MOPS buffer (Invitrogen). 10 μg sample (added SDS loading buffer; Invitrogen) was analyzed. If indicated, ethidium bromide was also used in gel staining for native gel samples. Otherwise, gels were photographed before and after staining with Coomassie Blue using Alphalmager (Biosciences) imaging system and UV or white light.

ICP-OES measurements: The CDDP content per CPMV was determined using an ICP-OES (Perkin-Elmer ICP-OES 3300 DV) located in the Geology Department at Kent State University.

Results

Loading CPMV nanoparticles with fluorescent dyes through infusion and nucleic-acid-mediated retention. CPMV was propagated in *Vigna unguiculata* plants and purified using previously described procedures. Wen et al., J Vis Exp, 69 (2012). Typical yields were 100 mg of pure CPMV from 100 g of infected leaf material. The purity of CPMV preparation was assessed using size exclusion chromatography (SEC) and transmission electron microscopy. Samples were stored in 0.1 M potassium phosphate buffer pH 7.0 at 4° C.

To investigate the possibility and efficiency of dye-loading into the CPMV carrier system through infusion, the following fluorophores were chosen: DAPI (4',6-diamidino-2 phenylindole), propidium iodide (PI, 3,8-diamino-5-[3-(diethylmethylammonio)propyl]-6-phenylphenanthridinium diiodide), and acridine orange (AO, 3,6-Bis(dimethylamino)acridinium chloride), all of which are cationic, nucleic acid intercalating, fluorescent stains.

Figure 2:
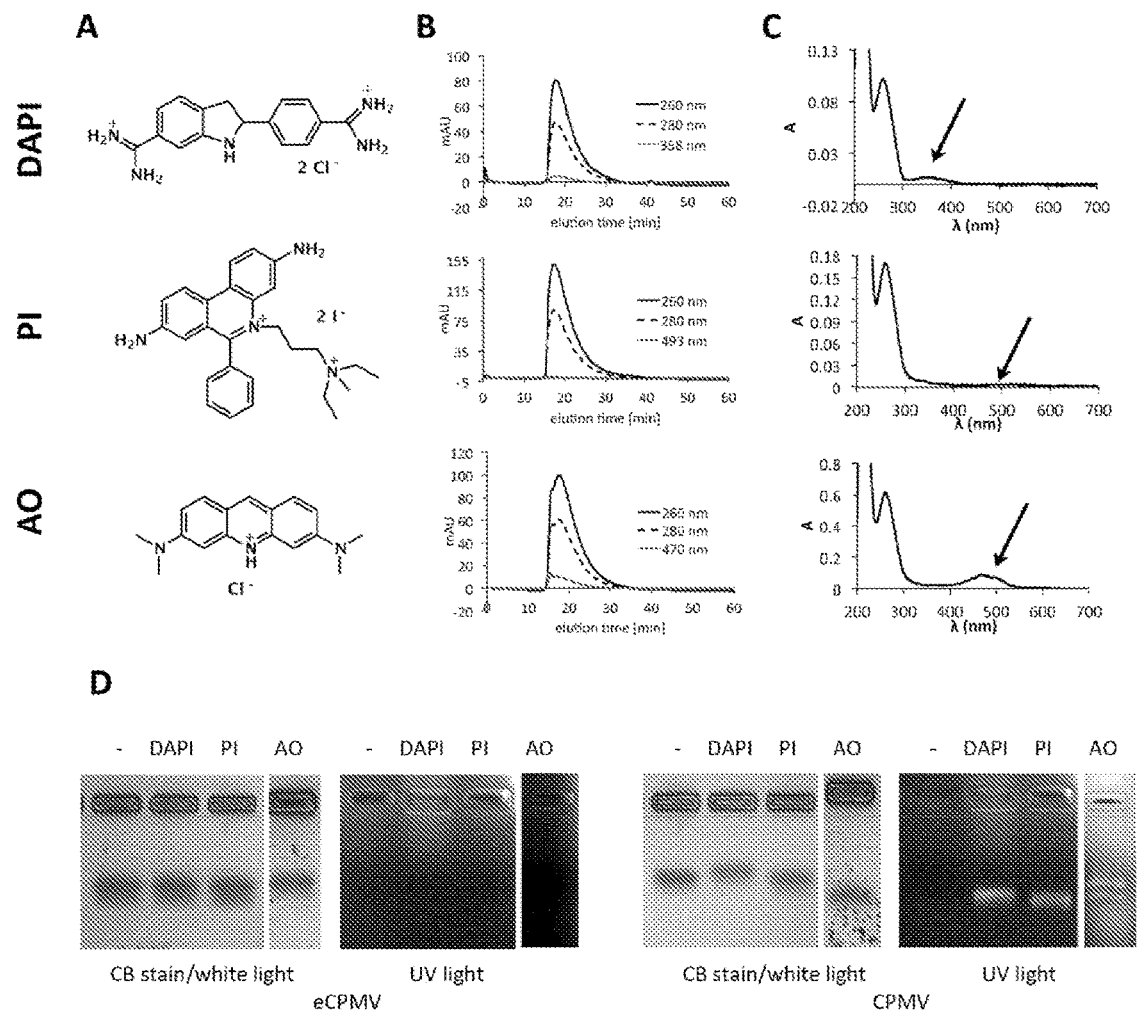
FIG. 2 provides chemical structures, graphs, and gel images showing A) Structure of DAPI (4',6-diamidino-2-phenylindole), propidium iodide(PI, 3,8-diamino-5-[3-(diethylmethylammonio)propyl]-6-phenylphenanthridinium diiodide), and acridine orange (AO, 3,6-bis(dimethylamino) acridinium chloride). B) Size exclusion chromatography of CPMV-DAPI, CPMV-PI, and CPMV-AO shows the typical elution profile of intact CPMV, co-elution of the dyes indicates loading. C) UV/visible spectra of CPMV-DAPI, CPMV-PI, and CPMV-AO showing the CPMV typical peak at 260 nm and the dye-specific absorbance peak at 358, 493, and 470 nm, respectively. D) Native agarose gel electrophoresis of CPMV and eCPMV after incubation with DAPI, PI, AO. The gels were visualized and documented under UV light and then stained with Coomassie blue and photographed under white light.

Intact CPMV nanoparticles were incubated in a bathing solution containing the fluorophores (DAPI, PI, or AO, FIG. 2A) at various molar excesses (1,000, 2,000, 5,000, 10,000, and 50,000 dyes per 1 CPMV), incubation times were varied between one hour to overnight reactions. After completion, the reaction mix was extensively purified through several rounds of dialysis and spin filter centrifugation to remove excess reagents and dyes were quantified based on UV/visible absorbance spectroscopy (see materials and methods). Overall, it was found that an excess of 10,000 dyes: 1 CPMV nanoparticle and incubation for one hour gave most reproducible results in terms of yield of recovered CPMV and dye-loading efficiency. Recovery of purified, dye-loaded CPMV was 50-70% of the starting material. Structural integrity and loading with dye was confirmed using SEC, UV/visible spectroscopy, and native gel electrophoresis (FIG. 2B-D).

Size exclusion chromatography using FPLC and a Superose 6 column showed the typical elution profiles for intact CPMV nanoparticles: CPMV loaded with DAPI, PI, and AO elute at 17.9 min, 17.5 min, and 17.6 min (FIG. 2B), respectively, which is in agreement with elution profiles for native CPMV (not shown). The ratio of A260 nm:A280 nm provides additional information of the integrity of CPMV preparations, the peak at 260 nm is from the absorbance of encapsulated nucleic acids and absorbance at 280 nm reflects the protein capsid. Pure and intact CPMV preparations have an A260 nm:A280 ratio of 1.7±0.1. CPMV DAPI, CPMV-PI, and CPMV AO, each show A260 nm:A280 nm ratio of 1.7. For CPMV-AO, SEC elution profiles indicate a shoulder at 15.7 min, indicating that some aggregation occurred. This was a reproducible phenomenon and also observed in native agarose gel electrophoresis. Although a small fraction of the CPMV formulation appeared to aggregate, the main peak is indicative of non-aggregated CPMV-AO nanoparticles. The latter was also confirmed by native agarose gel electrophoresis. FPLC elution profiles indicate successful loading of dyes: co-elution of the DAPI, PI, and AO as measured at 358 nm, 493 nm, and 470 nm, respectively, indicates loading of the dyes into the CPMV nanocarrier (see also UV and native gel data below). PI absorbance is low, which is reflected by its low extinction coefficient with $\varepsilon PI(493\ nm)=5,900\ M^{-1}cm^{-1}$, compared to DAPI and AO, which have extinction coefficients with values of $\varepsilon DAPI(358\ nm)=24,000\ M^{-1}cm^{-1}$ and $\varepsilon AO(470\ nm)=43,000\ M^{-1}cm^{-1}$.

The degree of dye-loading was quantified using UV/visible spectroscopy and the concentration ratio of dye: CPMV (see materials and methods). The inventors found that CPMV could be loaded with 130±10% DAPI or PI and 155±10% AO; the increased AO ratios may be due to an overestimate based on the aggregated fraction in the preparation. Longer incubation times or larger excess of dye: CPMV did not yield more efficient loading, thus indicating that CPMV is saturated with dyes at a loading capacity of 130-155 dyes per CPMV nanoparticle.

Loading of the fluorescent cargos inside the CPMV carrier was further confirmed using native gel electrophoresis. RNA-containing CPMV and RNA-free empty eCPMV nanoparticles (Saunders et al., Virology, 393, 329-37 (2009)) were incubated with dyes, purified to remove unbound dyes, and then analyzed using agarose gels under native conditions. After separation of the intact (e)CPMV dye complexes, gels were visualized under UV light or stained with Coomassie and imaged under white light (FIG. 2D). CPMV nanoparticles appear as a double-band on native agarose gels; this band pattern reflects a proteolytic cleavage of the small (S) coat protein: CPMV particles with cleaved S have a higher mobility in the gel compared to fractions that contain the full length S protein. Depending on the preparation, the double bands may be more or less profound on the gel. Steinmetz et al., 8, 1131-1136 (2007). The overall band pattern is consistent with intact eCPMV nanoparticles. Furthermore, native gel electrophoresis data indicate that dyes DAPI, PI, and AO were successfully loaded into the CPMV capsids. Uptake of dye into RNA-free eCPMV nanoparticles was not apparent, thus indicating that the loading is dependent on the RNA molecules.

Chemical reactivity of dye-loaded CPMV nanoparticles. The chemical reactivity of the CPMV surface lysine side chains after cargo-loading was then investigated. Bioconjugation and addressability of the exterior CPMV surface is well known. CPMV nanoparticles display 300 reactive Lys side chains; all of which can be labeled using N-hydroxysuccinimide (NHS) active chemical modifiers and forcing conditions (high excess and long incubation periods. Chatterji et al., Chem Biol, 11, 855-863 (2004). Using standard labeling protocols, typical labeling efficiency lies between 60-120 labels per CPMV. Here, a standard labeling protocol was used (see methods), a NHS active ester of the fluorophore AlexaFluor555 (A555), and DAPI-loaded CPMV or native CPMV. Native and DAPI-loaded CPMV nanoparticles showed similar reactivity resulting in covalent display of 80±10% A555 dyes per CPMV and CPMV-DAPI nanoparticle, respectively. The degree of labeling was determined using UV/visible spectroscopy and the A555 specific extinction coefficient.

Figure 3:
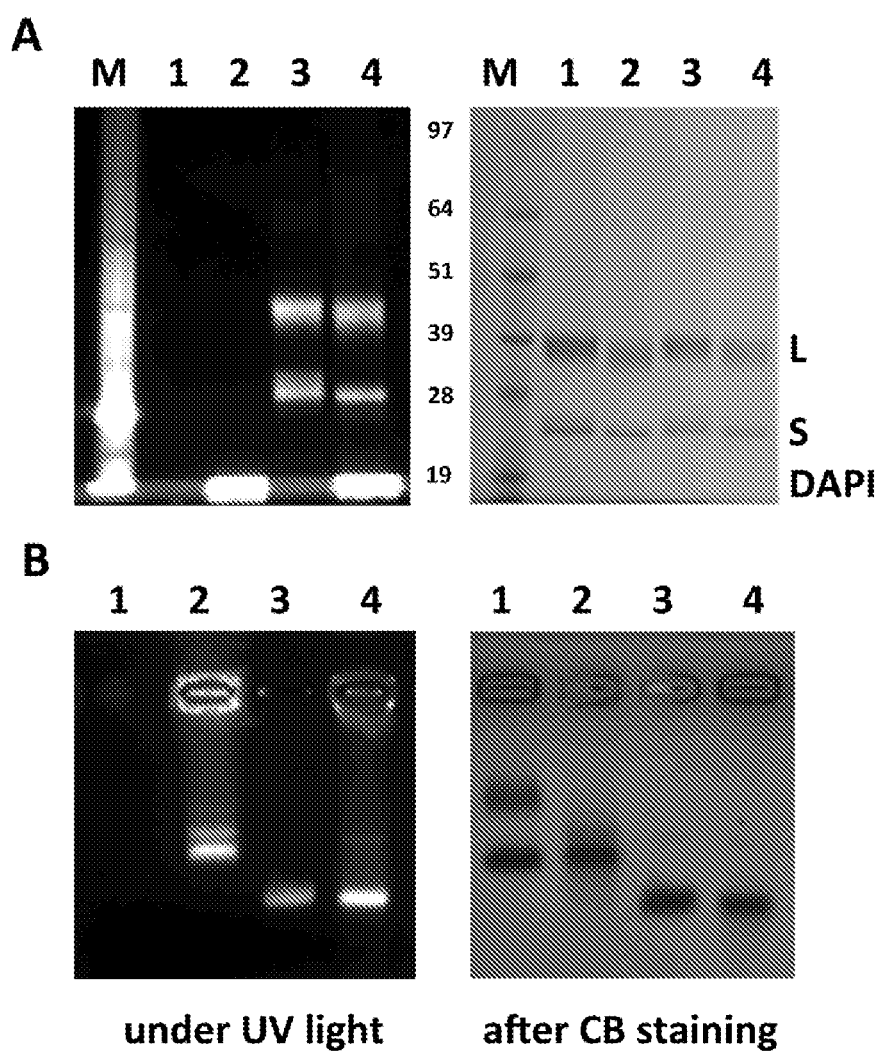
FIG. 3 provides images showing the electrophoretic separation of CPMV-DAPI and their coat proteins. A) Denaturing gel electrophoresis using a NuPAGE gel and B) native gel using an agarose gel. 1=CPMV, 2=CPMV-DAPI, 3=A555-CPMV, 4=A555-CPMV-DAPI, M=molecular weight standard; the bands are labeled in the center of the gels (in kDa). Gels were visualized under UV light and under white light after Coomassie blue (CB) staining.

Native and denaturing gel electrophoresis techniques were used to confirm that DAPI was non-covalently loaded into the interior cavity of CPMV, complexed with the nucleic acids, and that A555 was covalently linked to the CPMV coat proteins (FIG. 3). Gels were visualized under UV light and under white light after Coomassie staining. In denaturing gels, CPMV coat proteins are separated and visualized. The process of denaturing releases the encapsulated cargo (here DAPI), which is, based on its small molecular weight (MW=277.324 gmor$^{-1}$), detectable in the buffer front at the bottom of the gel (FIG. 3A, lanes 2 and 4). The fluorescent appearance of coat proteins for A555-CPMV and A555-CPMV-DAPI (FIG. 3A, lanes 3 and 4) indicates covalent modification of both the small (S, 24 kDa) and large (L, 42 kDa) coat protein of CPMV.

In native agarose gels, intact CPMV nanoparticles are analyzed. DAPI-loaded and A555-labeled CPMV formulations appear fluorescent under UV light; free dye is not detected for any of the preparations; indicating that DAPI is stably encapsulated and not released during migration in the gel matrix (FIG. 3B). The migration pattern toward the anode differs for the DAPI-loaded versus A555-labeled CPMV: DAPI is encapsulated on the interior of the CPMV particles, and alters the electrophoretic mobility only minimally. In contrast, A555, a non-charged molecule, is covalently attached to surface lysines. The A555-CPMV formulation displays fewer positive charges on its surface compared to native CPMV, and thus has enhanced mobility toward the anode.

CPMV particles have two electrophoretic forms; this is due to cleavage of the highly charged C-terminus of the S protein. In denaturing gels this can be observed by the double band that appears for the S protein (FIG. 3A). In the native gel both electrophoretic forms are detected for the native CPMV preparation (FIG. 3B, lane 1). For DAPI-loaded and chemically-modified A555-labeled CPMV preparations, only the fast electrophoretic form appears (FIG. 3B). This phenomenon previously; it is possible that labeling and purification conditions, further promote cleavage of the S protein.

Overall, data indicate that the chemical addressability for cargo-loaded CPMV nanoparticles is similar to that of native CPMV, allowing for the production of dual-modified CPMV carrier systems.

Example 2: Cargo Delivery to Cells

Tissue Culture: HeLa cells (cervical cancer) were obtained from ATCC®, and cultured and maintained in Minimum Essential Media (MeM) supplemented with 10% (v/v) FBS, 1% (w/v) penicillin-streptomycin, 1% (w/v) glutamine at 370 C and 5% $CO_2$. PC-3 cell line (prostate cancer) was obtained from ATCC® and maintained in Dulbecco's modified Eagle medium-F12 (DMEM/F12) that contained 10% (v/v) FBS, 1% (w/v) penicillin-streptomycin, 1% (w/v) glutamine at 370 C and 5% $CO_2$. HT-29 cells (colon cancer) were obtained from ATCC®, and cultured and maintained in RPMI 1640 medium supplemented with 10% (v/v) FBS, 1% (w/v) penicillin-streptomycin, 1% (w/v) glutamine at 37° C. and 5% $CO_2$. All culture media reagents were purchased from Invitrogen.

Confocal Microscopy: Cellular uptake of CPMV: HeLa, PC-3, or HT-29 cells (25,000 cells/well) were grown for 24 hours on glass coverslips placed in an untreated 24-well plate in 200 µL media (see above) at 370 C, 5% $CO_2$. Cells were washed and 0488-CPMV, 0488-CPMV-PF, 0488-CPMV-CP (at 10 µg/well) were introduced in 100 µL of corresponding media, incubated for three hours, and then washed with saline to remove any unbound particles. Cells were fixed for five min at room temperature using DPBS containing 4% (v/v) paraformaldehyde and 0.3% (v/v) glutaraldehyde. Cell membranes were stained using 1 µg/mL wheat germ agglutinin (WGA) conjugated with AlexaFluor-555 (WGA-A555; Invitrogen) in 5% (w/v) goat serum (GS) for 45 min at room temperature in dark followed by subsequent washing with DPBS (Invitrogen). Nuclei were stained with DAPI (MP Biomedicals, 1:7500) for five min Cells were washed with DPBS in between each staining step. Coverslips were then mounted onto glass slides using mounting media (Permount, Fisher Chemicals) and sealed using nail polish. Confocal images were captured on Olympus FluoView™ TM FV1000 LSCM and data processed using Image J 1.44o software, which is available on the internet.

Co-localization of CPMV with endolysosomes: Native CPMV was used and stained using CPMV-specific antibodies. After incubation of HeLa cells with CPMV (as described above), cells were incubated with anti-CPMV antibodies (rabbit IgG, Pacific Immunology) at 1:200 dilution for 60 mM at room temperature. Endolysosomes were stained using a mouse anti-human LAMP-1 antibody (Biolegend, 1:200; 5% GS) for 60 min Secondary antibodies, goat anti-mouse-AlexaFluor 488 (secondary to LAMP-1 Ab) and goat anti-rabbit-AlexaFluor 555 (secondary to anti-CPMV Ab) at 1:500 dilutions (mixed together) were then used to label the primary antibodies for 60 mM DAPI staining and imaging was as described above.

Cellular uptake of CPMV-DAPI: HeLa cells (25,000 cells/well) were grown for 24 hours on glass coverslips placed on an untreated 24-well plate in 200 µL medium (see above) at 37° C., 5% $CO_2$. Cells were washed and (A555)-CPMV-DAPI (1.7 nM CPMV, 0.233 µM DAPI /well) introduced in 100 µL medium, and cells were incubated for one to three hours at 37° C. or 4° C., and then washed to remove any unbound CPMV particle with saline. Cells were fixed and stained with WGA-A488 (Invitrogen) as described above. CPMV was visualized either based on covalently-attached A555 dye or stained using anti-CPMV specific antibodies. Confocal images were captured and analyzed as described above.

Fluorescence activated cell sorting (FACS): HeLa and HT29 cells were grown to confluency, and collected using enzyme-free Hank's based Cell Dissociation Buffer, and distributed in 200 µL, aliquots at a concentration of $5 \times 10^5$ cell/mL in V-bottom 96-well plates. Cargo-loaded and dye-labeled CPMV samples (3 µg and 15 µg/ per well) were added to cells and incubated for 3 h at 37° C., 5% $CO_2$. The cells were washed two times in FACS buffer (PBS solution of 1 mM EDTA, 25 mM HEPES at pH 7, 1% FBS (v/v)) and fixed in 2% (v/v) formaldehyde in FACS buffer for 10 minutes at room temperature. Cells were washed and resuspended in FACS buffer and analyzed using a BD LSR II flow cytometer. At least 10,000 events (gated for live cells) were recorded. Experiments were repeated at least twice and triplicates of each sample were measured. Data were analyzed using FlowJo 8.6.3 software.

Cell viability assay: XTT Cell Proliferation Assay Kit (ATCC®) was used to determine cell viability. For XTT assay, HeLa, HT-29, and PC-3 cells were seeded on a 96-well plate (25,000 cells/well; 100 µl MEM/well), incubated for 24 h at 37° C., 5% $CO_2$, washed twice, and then incubated in 100 µl MEM containing varying concentrations of cargo-loaded CPMV samples and respective controls (free CPMV and free drug). Time course studies were conducted: cells were treated with candidate formulation for 1 day, washed with saline to remove any unbound particles and drug, and placed in fresh medium for further incubation for 24 hours, 72 hours, and five days, prior to measuring cell viability. At the end of each incubation period, 50 µl of XTT reagent (reconstituted as per instructions in the kit) was added to each well and the plates were incubated for another 2-3 h for color development. The absorbance at 450 nm and 650 nm was then recorded on TECAN Infinite® 200 PRO multimode plate reader; data were analyzed as recommended by the supplier. All assays were analyzed in triplicates and repeated at least twice, and data were analyzed using Microsoft Excel software.

Cargo-delivery to cells. DAPI-loaded CPMV nanoparticles were chosen to study their fate in vitro and evaluate cargo delivery to cells. DAPI is a dye commonly used in tissue culture to stain the cell nuclei. The molecule is cell membrane permeable; it diffuses into the nucleus where it intercalates into the DNA. When bound to DNA, DAPI produces a blue fluorescence with excitation at about 360 nm and emission at 460 nm. Kapuscinski et al., Biotech Histochem, 70, 220-233 (1995). The inventors hypothesized that CPMV carrying DAPI would bind and internalize into cells via endocytosis to localize within the endolysosomal compartment, where the CPMV carrier is degraded, and DAPI released to target the nucleus.

For the studies, the human cervical cancer cell line HeLa was used. CPMV-HeLa cell interactions are well characterized. The inventors and others have previously reported that CPMV nanoparticles interact with mammalian cells via interaction with surface-expressed vimentin. Koudelka et al., J Virol 81, 1632-1640 (2007). This property can be utilized to target cancer cells, e.g. cervical, colon, and prostate cancer cells. In addition to vimentin-mediated internalization, other endocytotic pathways also could play a role in CPMV-cell interactions. CPMV binds and internalizes into cells via energy-dependent endocytosis and translocates into the endolysosomal compartment. Plummer E M and Manchester M, Molecular Pharmaceutics 10, 26-32 (2013)

Time and temperature-dependent cargo-delivery studies were performed: CPMV nanoparticles loaded with DAPI and covalently-labeled with A555 were incubated with HeLa for 10 mM versus 60 mM and at 4° C. versus 37° C. CPMV uptake was not apparent at 4° C.; this is consistent with previous studies reporting that CPMV uptake is an energy-dependent process. At 37° C. CPMV uptake was detectable after 60 mM incubation with HeLa cells and accompanied by DAPI fluorescence from the nucleus. DAPI-fluorescence from the CPMV carriers is not detectable, which can be explained by the fact that the DAPI is only weakly fluorescent when incorporated into RNA structures. Fluorescence from the nuclei indicates that DAPI is released from the CPMV carrier inside the cells allowing DAPI to diffuse into the nucleus, where it intercalates into the genomic DNA.

To confirm that DAPI is indeed released inside the cells as opposed to leaking out of the CPMV carrier in medium during the 60 min incubation time; a concentration-dependent study was conducted: a typical cell nuclei staining protocol makes use of DAPI at 20 mM concentration or higher. For delivery studies, the DAPI concentration was five magnitudes lower measuring only 0.2 µM DAPI. Cells incubated with free DAPI at 0.2 µM do not show any apparent fluorescent signals from the nuclei. In stark contrast, 0.2 µM DAPI delivered to cells via the CPMV carrier shows fluorescent signals from the nuclei within 60 min of incubation. This indicates that even though DAPI is a cell permeable dye, it enters cells more efficiently when delivered through the CPMV nanocarrier. Colocalization studies confirmed intracellular localization and translocation of CPMV into the endolysosomal compartment; this is indicated by co-localization with Lamp-1 marker.

Overall, this study indicates that cargo infused into CPMV, bound to the viral nucleic acid, can be efficiently delivered into cells. Structural changes and degradation of the CPMV carrier within the endolysosomes appear to trigger release of the cargo allowing for endolysosomal escape and targeting of the nucleus. These studies thus laid the foundation for drug delivery (see below).

Figure 4:
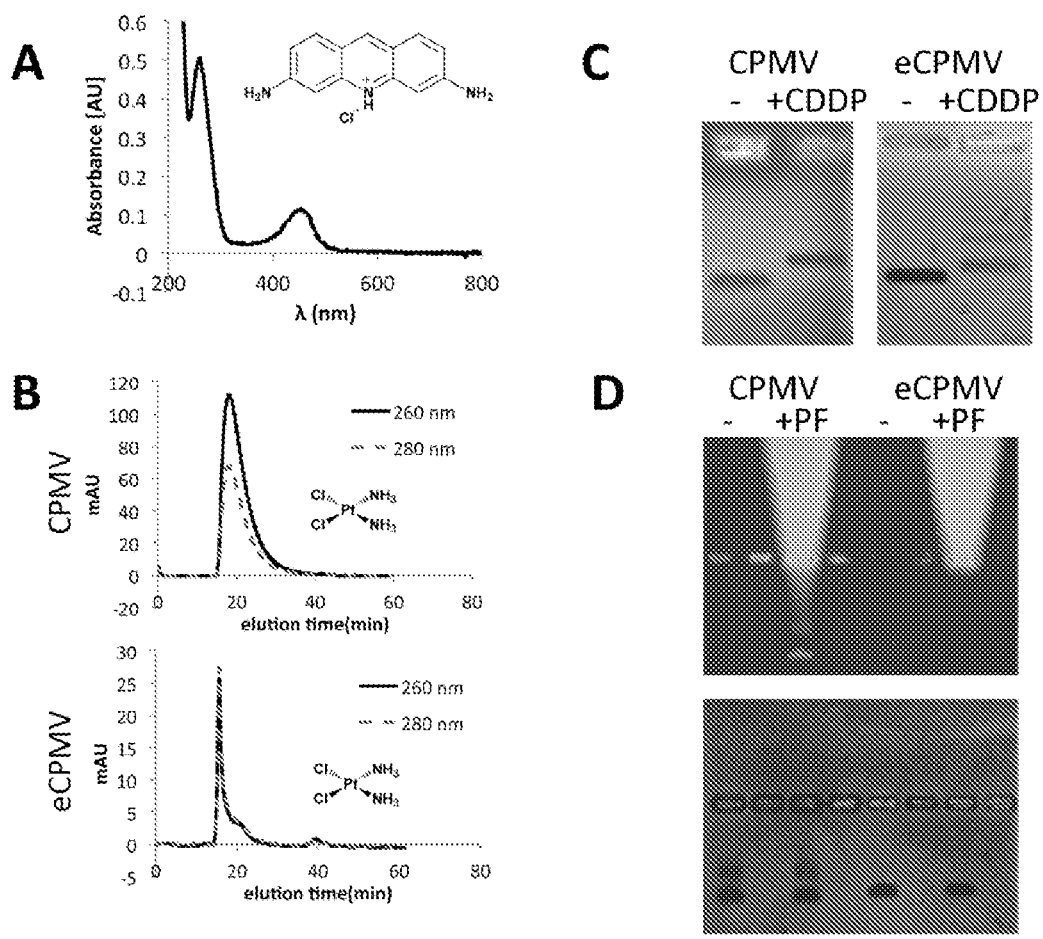
FIG. 4 provides graphs and gel images showing the characterization of drug-loaded CPMV. A) UV/visible spectroscopy of CPMV-PF showing the CPMV and proflavine-specific absorbance maxima at 260 nm and 450 nm B) Size exclusion chromatogram of CPMV-CDDP and eCPMV-CDDP. C) Native gel electrophoresis of CPMV and eCPMV with and without CDDP; gels were stained with Coomassie blue and photographed under white light. D) Native gel electrophoresis of CPMV and eCPMV with and without proflavine (PF) (it should be noted that non-purified samples were analyzed on the gel to show the migration pattern of free PF versus (e)CPMV); gels were documented under UV light, and then stained with Coomassie blue and photographed under white light. The bright bands in proflavine-positive samples indicate free dye that migrates towards the cathode in the electrophoretic field (on top).

Loading of drug molecules via infusion and nucleic acid retention. Next, drug loading into CPMV followed by drug delivery to cancer cells was investigated. Two drugs were chosen: proflavine (PF, 3,6-diaminoacridine hydrochloride) and CDDP (cisplatin or cis-dichlorodiammine platinum(II)) (FIG. 4). Proflavine is mostly known as a bacteriostatic with applications as topical antiseptic. Cytotoxic activity of proflavine and its derivatives (e.g. proflavine diureas) in cancer cells and tumors has also been reported. The antiproliferative activity has been related to proflavine intercalation into DNA. Sasikala WD and Mukherjee A, The journal of physical chemistry B, 116, 12208-12212 (2012). Although the use of proflavine, as well as other acridine derivatives, for modern chemotherapy may be controversial based on their inherent mutagenic properties, it served as a reasonable guest molecule for the studies.

As a second test drug, CDDP was chosen. CDDP is a cytotoxic drug used to treat various cancers; the drug is an alkylating agent that binds non-reversibly to DNA thereby causing crosslinking of DNA, which ultimately leads to apoptosis. DNA is the major target of CDDP, however, CDDP also has been found to bind to intracellular components and RNA (Gomez-Ruiz et al., Bioinorg Chem Appl, 2012, 140284 (2012)); the inventors thus speculated that loading into RNA-containing CPMV capsids might be possible.

First, loading of proflavine and CDDP into RNA-containing CPMV and RNA-free eCPMV nanoparticles was studied: intact eCPMV nanoparticles were incubated in a bathing solution containing the drugs at various molar excesses ranging between 1,000-50,000 drugs per 1 CPMV. After completion, the reaction mix was extensively purified through several rounds of dialysis and spin filter centrifugation to remove excess reagents. Proflavine loading was quantified based on UV/visible absorbance spectroscopy (FIG. 4A); CDDP loading was quantified using inductively coupled plasma emission optical spectroscopy (ICP-OES). According to results obtained from dye-loading, an excess of 10,000 proflavine or CDDP:1 CPMV nanoparticle was found to give the most reproducible results in terms of yield of recovered CPMV (50-70% of starting materials) and drug-loading efficiency: 180±10% CDDP and 140±10% proflavine.

To confirm intactness of the preparation and analyze drug loading further, SEC and native gel electrophoresis was performed. Proflavine loading was studied by native gel electrophoresis and imaging gels under UV light (detection of the fluorescent proflavine compound) and under white light after Coomassie blue staining (detection of the protein-based viral nanoparticles). Loading of proflavine was only observed using RNA-containing CPMV nanoparticles (fluorescent bands on UV light, FIG. 4D), non-specific uptake or interactions of proflavine with RNA-free eCPMV was not detectable by native gel electrophoresis (FIG. 4D).

CPMV and eCPMV were incubated with CDDP and purified samples were analyzed: SEC using FPLC and a Superose6 column showed the typical elution profiles for intact nanoparticles with CPMV-CDDP eluting at 17.4 min (A260:A280 nm=1.7). Interestingly, eCPMV-CDDP preparations appeared to be aggregated as indicated by a sharp elution peak at 15.4 min (FIG. 4B). Native gel electrophoresis was in agreement, lower mobility bands indicate eCPMV-CDDP aggregates (FIG. 4C), this was not apparent for CPMV-CDDP. The only difference between CPMV and eCPMV is the presence of the RNA genome. It appears that RNA stabilizes the formulation and prevents aggregation. The lower mobility of CPMV-CDDP versus native CPMV may be explained by the addition of two positive charges with each CDDP molecule loaded; the increased positive charge may reduce the mobility of the particles toward the anode.

Overall data indicate that both drugs tested, CDDP and proflavine, diffuse inside the CPMV carrier where they are retained through interaction with the encapsulated nucleic acids.

Figure 5:
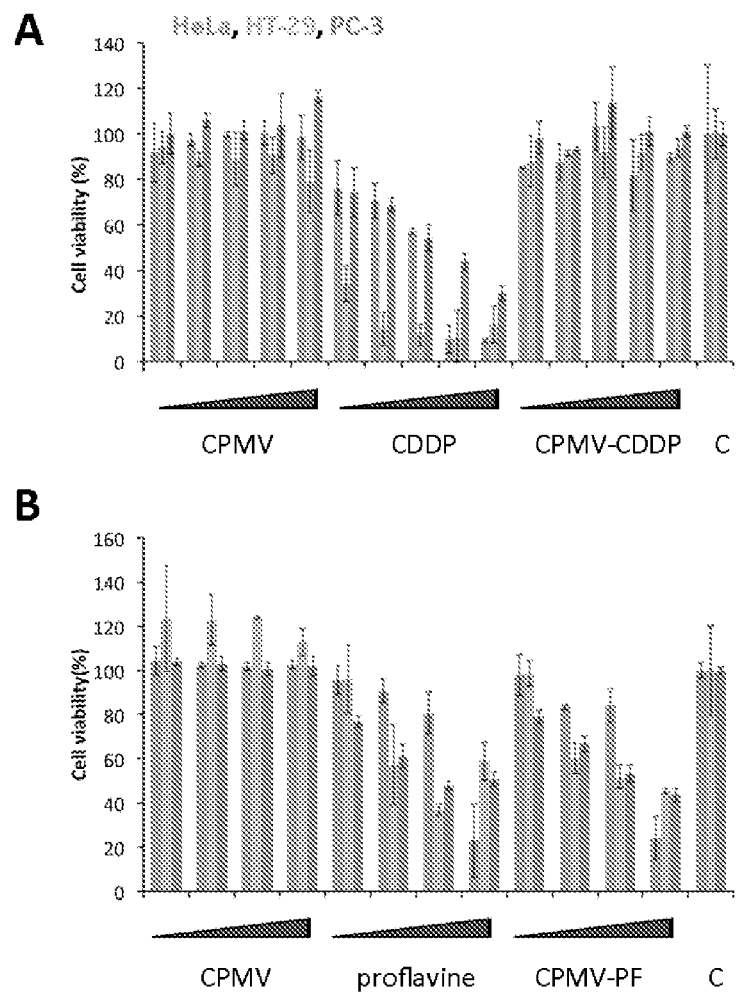
FIG. 5 provides bar graphs showing the results from cell viability assays. A) HeLa, HT-29, and PC-3 were exposed to CDDP and CPMV-CDDP at 6 µM, 9 µM, 12 µM, 21 µM, and 30 µM concentration of CDDP (equates to a CPMV concentration of 0.33 µM, 0.5 µM, 0.67 µM, 1.2 µM, and 1.7 µM) for 24 hours, and washed, and incubated for further 24 hours in tissue culture medium, prior to analysis of cell viability using XTT assay. C=untreated control cells. B) HeLa were exposed to proflavine and CPMV-PF at 0.3 µM, 0.6 µM, 1.8 µM, and 2.9 µM concentration of proflavine (equates to a CPMV concentration of 0.002 µM, 0.004 µM, 0.012 µM, and 0.02 µM) for 24 hours, and washed, and incubated for further 24 hours in tissue culture medium, prior to analysis of cell viability using XTT assay. C=untreated control cells. HT-29 and PC-3 were exposed to proflavine and CPMV-PF at 1.46 µM, 3.07 µM, 6.13 µM, and 16.06 µM concentration of proflavine (equates to a CPMV concentration of 0.010 0.021 0.042 and 0.11 µM) for 24 hours, and washed, and incubated for further 24 hours in tissue culture medium, prior to analysis of cell viability using XTT assay. C=untreated control cells. For each triple bar shown, the results on the left are for HeLa, the results in the middle are for HT-29, and the results on the right are for PC-3.

Drug delivery, release, and cell killing. Next, proflavine and CDDP delivery to cancer cells was evaluated. A panel of cancer cells was used for these studies: HeLa (cervical cancer cells), HT-29 (colon cancer cells), and PC-3 (prostate cancer cells). Drug delivery and cell killing was evaluated (FIG. 5).

CPMV-PF formulations show drug efficacy similar to that observed for free proflavine (FIG. 5B). In HeLa cells, free proflavine and CPMV-PF showed response with $IC_{50}$ between 1.8 µM and 2.9 µM proflavine concentration. In HT-29 and PC-3 cells, the $IC_{50}$ was determined at 6.13 µM for free and delivered drug. The CPMV carrier itself is not toxic to cells (FIGS. 5A and 5B). In contrast to CDDP, proflavine is an intercalating agent and this process is reversible, and the data indicate that after the CPMV-PF complex enters the cells, the drug is released inducing cell toxicity (FIG. 5B).

Free CDDP showed the expected cytotoxicity in each cell line tested; cell killing efficiency varied between cell lines with $IC_{50}$ values of 12-21 µM for HeLa cells, 6 µM for HT-29 cells, and 30 µM for PC-3 cells, which could be explained by different physiology and growth rates (FIG. 5A). However, cell killing was not apparent studying CPMV-CDDP complexes over a range of concentrations and incubation times. CDDP binds to DNA via a non-reversible process inducing crosslinks. The cell viability assay indicated that CDDP loading into CPMV renders the drug non-active. Time-course studies were conducted over five days; even after such long incubation times, cell killing was not observed. The fact that cell killing is not observed using the CPMV-CDDP formulation could be explained by the non-reversible CDDP-nucleic binding mechanism; it is also possible that the drug is released but does not target the nucleus, however this may be less likely because CDDP is a membrane permeable drug.

Figure 6:
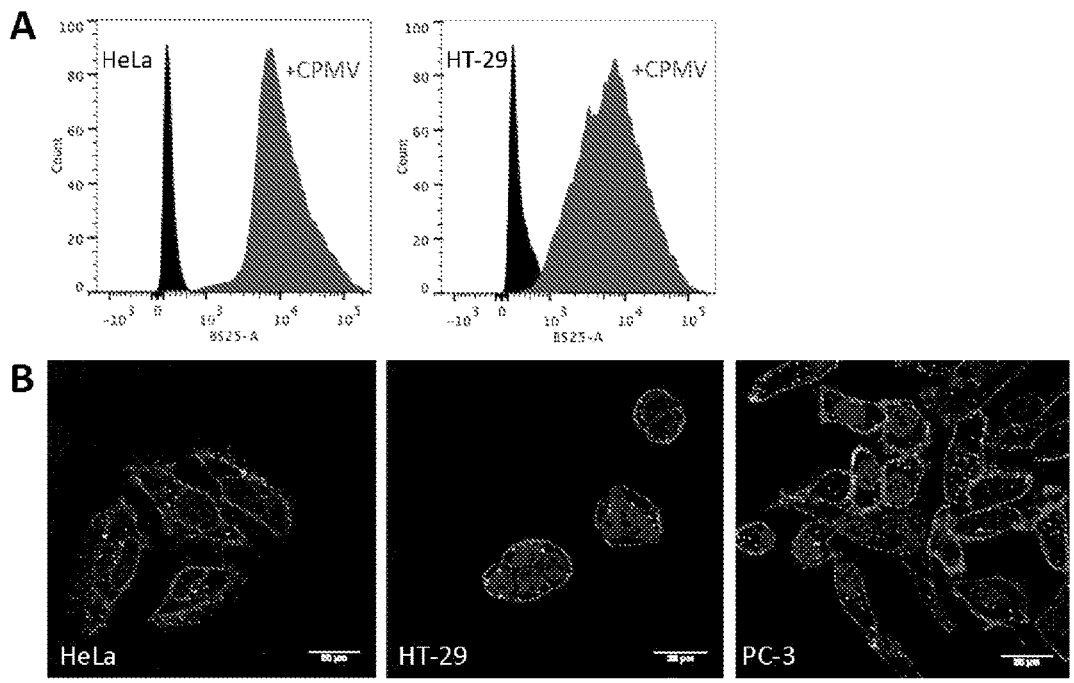
FIG. 6 provides graphs and images showing A) Cell binding of A555-CPMV-PF to HeLa and HT-29 cells after 60 min exposure. For these experiments cells were collected using non-enzymatic cell dissociation buffers to avoid the natural CPMV receptor being cleaved off the cell surface; a collection of PC-3 cells was not achieved using this method. B) Confocal microscopy images of HeLa, HT-29, and PC-3 cells after incubation with A555-CPMV-PF. The scale bar is 20 µm.

Flow cytometry and confocal microscopy were used to confirm uptake of drug-loaded CPMV in HeLa, HT-29, and PC-3 cells. For these studies, dual-modified drug-loaded and dye-labeled CPMV nanoparticles were produced. First, the drug was loaded through infusion; second, A555 was covalently attached using an NHS ester and targeting lysine side chains. SEC, UV/visible spectroscopy, and native gels confirmed the integrity of dual-modified CPMV; 100±10% A555 were attached per CPMV-PF. Cell data confirmed binding (FIG. 6A) and uptake of CPMV into HeLa, HT-29, and PC-3 cells (FIG. 6B), this is consistent with previous reports: HeLa, HT-29, and PC-3 express surface vimentin, allowing CPMV to target, bind and get taken up into the cells. In summary, it was demonstrated that CPMV nanoparticles can be efficiently labeled with therapeutic cargos, and the natural CPMV-vimentin specificity enables targeting, uptake, and cargo delivery.

Discussion

Nanoparticles in drug delivery. Nanoparticles are potentially useful for medical applications because they can be tailored to partition cargos between diseased and healthy cells and tissues. Diverse classes of materials are currently being considered; these include synthetic, man-made materials as well as natural nanomaterials, e.g. protein cages and capsids formed by viruses. Each class of nanomaterial offers distinct advantages and disadvantages. CPMV has many favorable properties for use as a nanocarrier. CPMV nanoparticles are non-pathogenic, non-toxic, and biodegradable in mammals at dosages of up to 100 mg ($10^{16}$ CPMVs) per kg body weight. CPMV nanoparticles are 30 nm in size; this size regime is ideal for cell targeting and uptake. Furthermore, based on their small size, CPMV has high likelihood to penetrate tissues more effectively compared to, larger micelles or liposomes. CPMV is monodisperse, and its structure known and amenable with atomic resolution. CPMV can be engineered with targeting ligands, drugs and/or imaging molecules at the exterior and interior surface using genetic engineering or bioconjugation protocols. Wen et al., Biomacromolecules 13, 3990-4001 (2012). Finally, CPMV nanoparticles are stable under various solvent, pH, and temperature conditions.

The inventors have demonstrated that cargos are released efficiently upon targeting of the endolysosome. A previous study delivered the chemotherapeutic molecule doxorubicin; in this case the drug was covalently introduced into the nanocarrier. Aljabali et al., Molecular Pharmaceutics, 10, 3-10 ((2013). It appears that CPMV is metabolically cleared from cells within a few days. The slow processing of the CPMV nanoparticles inside the endolysosome results in delayed drug release when the cargo is conjugated via a covalent mechanism. In contrast, it is reported here that cargos stably loaded via infusion technique were released quickly upon cell entry. For example, DAPI delivered by CPMV was detectable in the nucleus after 60 min exposure. It is possible that conformational changes in the capsid structure are induced upon entry into the acidic environment of the endolysosomal compartment, and thus inducing cargo release and eventual degradation of the carrier material. Based on its biology and natural affinity to surface expressed vimentin, CPMV provides an interesting carrier system to deliver cargos to vimentin-positive (cancer) cells. Besides all its advantages it should be noted, that a potential disadvantage of the protein-based carrier systems is that the repetitive coat proteins can induce immunogenicity, but this can be overcome by PEGylation.

Modification of virus-based materials. Based on the versatility of virus-based materials as carrier systems, the inventors and others have reported various modification techniques to functionalize the carriers with cargos and/or targeting ligands. A majority of efforts have focused on genetic and chemical modification. Pokorski J K and Steinmetz N F, Mol Pharm, 8, 29-43 (2011). Non-covalent techniques such as infusion have several advantages. While genetic engineering is only applicable to amino acid-based compounds, infusion-based cargo-loading is, at least theoretically, applicable to any material, including peptides, organic fluorophores, contrast agents, or chemotherapeutic drugs. Furthermore, infusion-based methods do not alter the composition or structure of the cargo; in contrast covalent modification can introduce alternations to the cargo rendering it less or non-active. Metabolic degradation and/or structural changes of the CPMV carrier within the endolysosomal compartment allow cargo-release without the need of introduction of release mechanisms, which could further hamper the functionality of the cargo. Finally, some genetic and/or chemical modifications can destabilize the protein structure. Modifications are not required for infusion-based cargo loading. Intact and native CPMV nanoparticles are used; which means that no structural changes are made to the virus-based carrier.

A few non-covalent VNP modification strategies have been developed and tested, for example cowpea chlorotic mottle virus (CCMV) was used to complex lanthanides at the interface of coat protein subunits. Under physiological conditions $Ca^{2+}$ ions are bound to these sites. $Ca^{2+}$ ions can be replaced with $Gd^{3+}$ or $Tb^{3+}$ cations; resulting in binding of 180 lanthanides. Basu et al., J Biol Inorg Chem 8, 721-725 (2003). These complexes could be potentially useful for magnetic resonance imaging applications. Similarly, the lanthanides $Gd^{3+}$ and $Tb^{3+}$ were infused and entrapped into CPMV particles making use of the encapsidated nucleic acids. Around 80±20 $Gd^{3+}$ and $Tb^{3+}$ ions can be stably bound and trapped inside CPMV based on RNA interactions. Prasuhn et al., Chem Commun 12, 1269-1271 (2007).

Infusion of small guest molecules into CPMV, as reported here, presents a convenient means of loading cargos into RNA-containing CPMV nanoparticles. The requirement for the cargo is that is has positive charges and/or affinity toward nucleic acids. To enable release, the interaction with nucleic acids must be reversible (see FIG. 5). CDDP binds nucleic acids via acetylation and therefore can be bound to but not released from CPMV. In contrast, nucleic acid intercalating molecules such as DAPI and proflavine bind to CPMV carriers via a reversible mechanism and thus can be released inside cells (see FIG. 5).

The inventors demonstrated that cargo molecules were stably bound inside RNA-containing CPMV nanoparticles; non-specific loading into eCPMV nanoparticles was not observed (see FIGS. 3 and 4). The formulations remained structurally sound and the guest molecules were stably encapsulated for several weeks upon storage under refrigeration in phosphate buffered saline solution at physiological pH. Cargo release in medium and during electrophoresis was not observed. Upon entry into the endolysosome, efficient release over relatively short time scales is triggered: it was indicated that DAPI was released within 60 min of exposure. Further, the $IC_{50}$ of CPMV-PF was comparable to that of free proflavine, further indicating efficient release (see FIG. 5).

RNA-containing CPMV nanoparticles are non-infectious toward mammalian cells, and therefore can be considered as safe. From an agricultural point of view, of course, RNA-containing nanoparticles are infectious toward legumes, such as black-eyed peas. To produce cargo-loaded CPMV-based nanoparticles that are safe from an agricultural point of view, one could consider the following strategy: three forms of CPMV nanoparticles can be isolated from infectious leaves by isopycnic centrifugation on density gradients. The three components have identical protein composition but differ in their RNA contents. The particles of the top (T) component are devoid of RNA, while the M and B components each contain a single RNA molecule, RNA-2 and RNA-1, respectively. Lomonossoff GP and Johnson J E, Prog Biophys Mol Biol 55, 107-137 (1991). While RNA-1 encodes the replication machinery, RNA-2 encodes the coat proteins. The presence of both RNA molecules is required to yield an infection and production of intact CPMV particles in the plants. One could consider separating B and M components for downstream medical applications to avoid any potential agricultural safety issues.

The chemical reactivity of cargo-loaded CPMV nanoparticles appears to be non-altered, which provides a foundation for the synthesis of dual-modified nanoparticles, e.g. encapsulating a therapeutic cargo while displaying contrast agents on the exterior surface—toward the development of theranostic devices.

Example 3: Delivery of PF-429242 to Treat LCMV Infection

Persistent viral infections (e.g. HIV, HBV, HCV) represent a significant source of morbidity and mortality with over 500 million persons infected worldwide. Using the LCMV model, the inventors identified dendritic cells (DC) and macrophages as key cell types where productive viral replication is required for persistent systemic infection. This observation highlights a potential "Achilles' heel" for persistent viral infection, where one may target specific cell types to eliminate overall persistent viral infection. The site-1 protease (SIP), a host protein required late in the viral life cycle to produce infectious lymphocytic choriomeningitis virus (LCMV), may be a key target for therapeutic approaches.

S1P is required for the life cycle of NIAID Category A & C priority pathogens (i.e., arenaviruses endemic in Africa and South America, Crimean-Congo hemorrhagic fever virus which is widespread across Africa, Europe and Asia). These viruses share a requirement for the host protease, SIP, to mature their glycoprotein. Rojek et al., J Virol., 84, 573-84 (2010). This event is required in vivo for the persistence of the prototypical arenavirus LCMV. This has been demonstrated using genetic manipulation of both the host and the virus. Popkin et al., Cell Host Microbe., 9:212-22 (2011). In addition to these studies, it was reported earlier this year that SIP is required for Hepatitis C virus (HCV) virus infection and its pharmacologic inhibition successfully blocked HCV replication. Blanchet et al., Antiviral Res., 95:159-66 (2012). Because of these diverse potential applications (dyslipidemias, anti-viral for numerous hemorrhagic fever viruses and HCV antiviral), S1P has become an increasingly attractive therapeutic target and therefore significant for further study.

Figure 7:
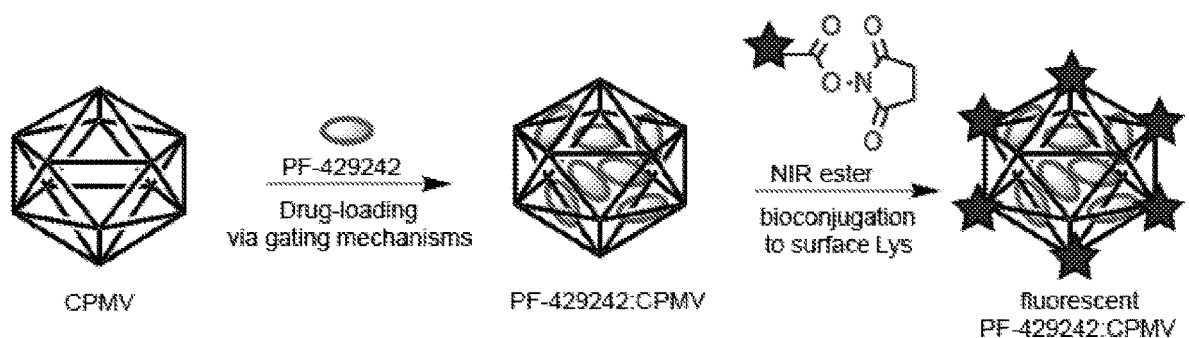
FIG. 7 provides a Reaction scheme: CPMV is loaded with PF-429242 using infusion method via pH-dependent gating mechanism; briefly at alkaline pH CPMV swells leading to pore opening, drug is infused, followed by neutralizing the pH. Fluorescent-labeling allows in vivo tracking of the formulation; CPMV is compatible with near-infrared dyes (NIR), using commercially available esters (e.g. Invitrogen™), labeling of CPMV's surface Lysine side chains will be carried out.

Therapeutic delivery using CPMV nanoparticles loaded with S1P inhibitor PF-429242 via infusion technique was demonstrated. The basic steps involved in preparing the loaded nanoparticles are shown in FIG. 7. CPMV has a natural tropism for DC and macrophages, and thus is an ideal candidate for targeted drug delivery targeting infectious disease. Treatment of persistent LCMV infection in vitro was demonstrated using PF-429242 loaded CPMV. LCMV is a model pathogen for persistent disease, but also LCMV itself and other members of the arenavirus family (all requiring S1P) are biologically significant pathogens, including NIAID Category A priority pathogens; therefore the chosen model has high clinical significance.

PF-429242 was dissolved in DMSO:buffer mixtures and added to CPMV at alkaline pH 8.0. This leads to a swelling of the viral capsids and pore-opening allowing for free buffer exchange between the bathing condition and interior cavity. Dialysis at neutral-to-acidic pH (pH 6.5) was performed to remove any excess drug and transition the capsids into the non-swollen, closed confirmation, therefore trapping the therapeutics inside the interior cavity. Ultracentrifugation techniques using sucrose or cesium chloride density gradients was used to purify distinct assemblies; it has been previously shown that CPMV nanoparticles and their conjugates can be separated on 10-40% (w/v) sucrose gradients. Steinmetz et al., Chembiochem, 8, 1131-6 (2007).

Figures 8A, 8B:
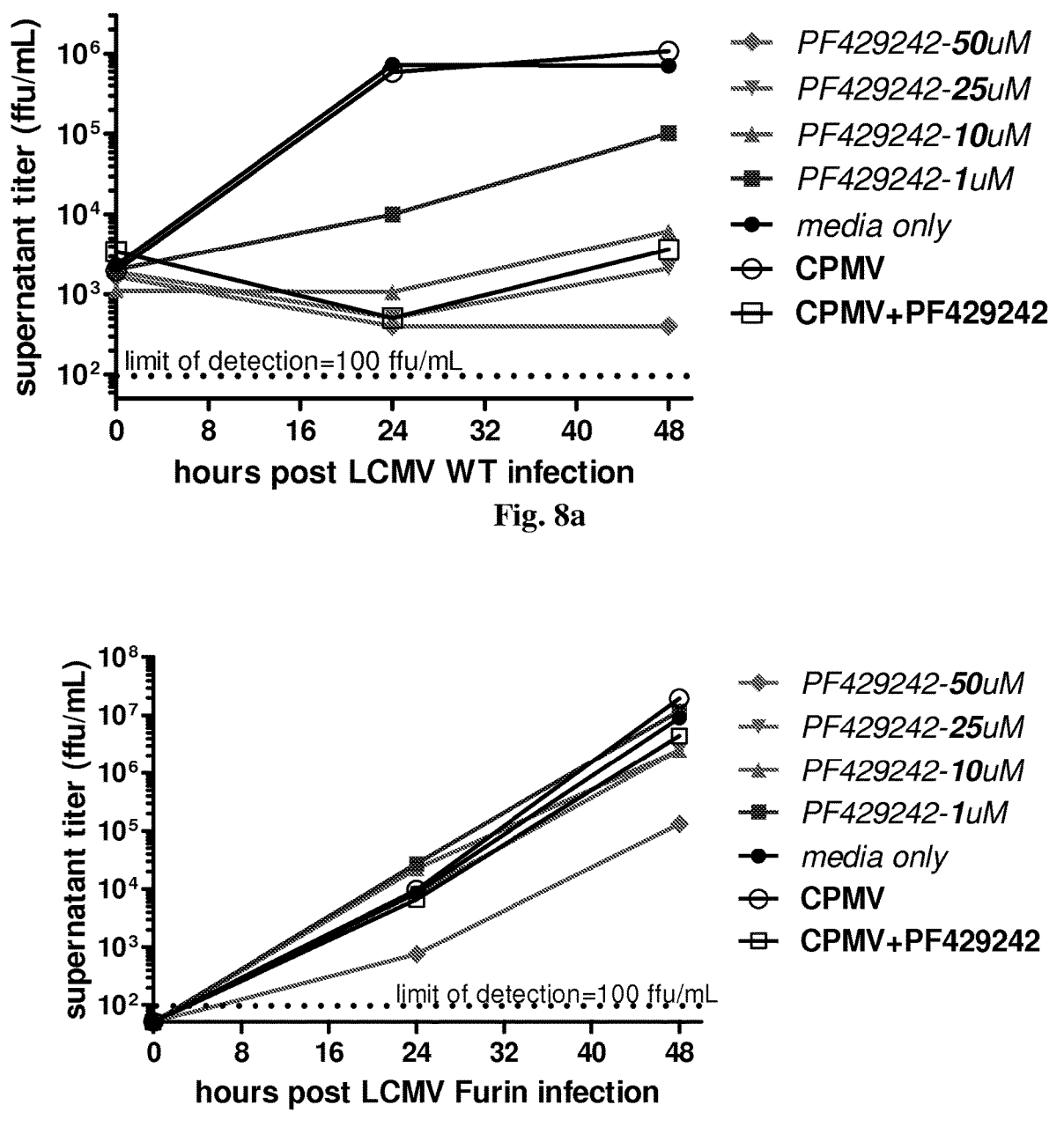

Hundreds of copies of drug molecules can be infused into the capsids using this method (Yildiz et al., J Control Release, 172(2), 568-78 (2013)); further the supporting data (see FIG. 8) support efficient drug loading and release of PF-429242 into and from CPMV in cells. BHK-21 cells were infected LCMV wildtype virus bearing the S1P recognition site RRLA or mutant "Furin" virus, which encodes a substitution at the S1P recognition site for RRLA→RRRR which is recognized by the furin protease and not by S1P. These recombinant viruses allow us to confirm specificity of PF429242 action for viral (vs. host) protein cleavage. Infected cells were treated with S1P inhibitor PF429242, CPMV, and CPMV:PF429242 (to produce 20 µM final concentration of the S1P inhibitor). Media was collected from these cultures at 24 and 48 hours post infection (hpi) and infectious titers were enumerated on Vero cells. This data establishes the efficacy of purified CPMV:PF-429242 post nanoparticle loading in a dose-dependent fashion (FIG. 8). Antiviral activity due to CPMV alone was not observed. Data indicate that drug delivery using CPMV is effective and specific (side effects or non-specific treatment was not observed using "Furin" virus).

Although the plant virus (CPMV) does not infect human cells, it delivers it cargo in macrophages and DCs, the same cells that are targeted by mammalian pathogens. In a way this approach could be described as biocleptic, in which the inventors borrow nature's approach and nanomaterials to deliver a potent S1P inhibitor to treat and clear persistent viral infections. The targeted delivery of high doses of S1P inhibitor specifically to DCs and macrophages is expected to increase the therapeutic efficacy, while reducing potential off-target effects or undesired clearance of the therapeutic.

Example 4: CPMV is Selective for Dendritic and Macrophage Cells

CPMV nanoparticles have a natural cell tropism to DC and macrophages. CPMV binds naturally to surface-expressed vimentin and the inventors have shown that this property can be exploited to target immune cells, specifically dendritic cells and macrophages (Gonzalez et al., PLoS One, 4, e7981 (2009)), sites of inflammation (Plummer et al., Nanomedicine (Lond)., 7:877-88 (2012)), and certain types of cancer cells (Steinmetz et al., Nanomedicine (Lond)., 6:351-64 (2011). CPMV enters human PMBCs within 4 hours and is selective for dendritic cell (DC) subsets and macrophage subsets. CPMV does not enter into natural killer (NK), T cells, B cells or other non-DC/macrophages during this time. This work indicates that CPMV is specific for myeloid DC in humans. CPMV enters human PMBCs within 4 hours and is selective for DC subsets and macrophage subsets. CPMV does not enter into NK, T cells, B cells or other non-DC/macrophages during this time. Myeloid DC are the predominant population that CPMV naturally targets and enters.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of loading a native plant picornavirus, comprising contacting a native plant picornavirus in solution with a molar excess of at least about 500 fold of a cargo molecule to load the plant picornavirus with the cargo molecule, and purifying the loaded plant picornavirus, wherein the cargo molecule is associated within the loaded plant picornavirus in a non-covalent manner, wherein the cargo molecule is loaded into the plant picornavirus via simple diffusion from the solution into the picornovirus.

2. The method of claim 1, wherein the plant picornavirus is a cowpea mosaic virus.

3. The method of claim 1, wherein the cargo molecule has an affinity for nucleic acid.

4. The method of claim 1, wherein the cargo molecule is an imaging agent.

5. The method of claim 1, wherein the cargo molecule is an antitumor agent.

6. The method of claim 1, wherein the cargo molecule is an antiviral agent.

7. The method of claim 1, wherein the plant picornavirus is in contact with the cargo molecule for at least an hour, and wherein the molar excess of cargo molecule is from about 5,000 to about 15,000.

8. The method of claim 1, further comprising the step of chemically modifying the lysine side chains on the surface of the plant picornavirus.

9. The method of claim 8, wherein the chemical modification is PEGylation.

10. The method of claim 8, wherein the chemical modification is attachment of a cell penetrating peptide or targeting ligand.

11. The method of claim 1, wherein the plant picornavirus is obtained from the extract of a plant infected by the plant picornavirus.

12. The method of claim 1, wherein the step of purifying the loaded plant picornavirus comprises dialysis of the plant picornavirus solution.

13. The method of claim 3, wherein the cargo molecule has a positive charge.

* * * * *